United States Patent [19]
Shih et al.

[11] Patent Number: 5,980,901
[45] Date of Patent: Nov. 9, 1999

[54] VIRAL DEFECTIVE INTERFERING PARTICLES AND USES THEREOF

[75] Inventors: Chiaho Shih, Houston; Ta-Tung Yuan, Galveston, both of Tex.

[73] Assignee: The Board of Regents of the University of Texas System, Austin, Tex.

[21] Appl. No.: 08/933,480

[22] Filed: Sep. 18, 1997

Related U.S. Application Data

[60] Provisional application No. 60/026,313, Sep. 18, 1996.
[51] Int. Cl.$^6$ .......................... A61K 39/29; A61K 39/12; C12N 7/00; C12N 7/04
[52] U.S. Cl. ...................................... 424/189.1; 424/188.1; 424/204.1; 424/225.1; 424/227.1; 424/93.6; 435/235.1; 435/236; 435/320.1
[58] Field of Search .............................. 424/188.1, 189.1, 424/204.1, 225.1, 227.1, 93.6; 435/235.1, 236, 320.1

[56] References Cited

PUBLICATIONS

Akarca et al. 1996 J Gen Virol. 76:1821–1826, Jun. 1996.
Gerin et al. Am J Pathology 81 (3) 651–658, Dec. 1975.
Nuesch et al. 1989 J Gen Virol. 70: 3475–3480, Dec. 1989.
Prince et al. 1996 J Viral Hepatitis 3 (1) 11–17, Jan. 1996.
Ruiz–Opazo et al. 1982 Cell 29 (1) 129–136, May 1982.
Wakita et al. 1991 J Clin Invest. 88:1793–1801, Dec. 1991.
Fultz et al 1982 Infect. Immun. 37(z) 679–686, Aug. 1982.

*Primary Examiner*—Frank C. Eisenschenk
*Assistant Examiner*—Mary K Zeman
*Attorney, Agent, or Firm*—Benjamin Aaron Adler

[57] ABSTRACT

The present invention provides a composition of matter comprising a defective interfering virus particle, wherein said particle naturally occurs in a human infection and wherein said particles has a naturally occurring core antigen internal deletion. Provided is a pharmaceutical composition, comprising defective interfering virus particle and a pharmaceutically acceptable carrier. Provided is a method for preparing defective interfering virus, comprising the steps of: (1) introduce a defective interfering virus and a complementing plasmid expressing a wild type virus core antigen and optionally containing a drug resistance gene, into a recipient cell; (2) selecting for stably transfected colonies; (3) growing the drug resistant cells and screening for the production of virus DNA replication; and (4) collecting defective interfering virus particles from the medium. Further provided is a vaccine, comprising a defective interfering virus particle.

9 Claims, 31 Drawing Sheets

VIRAL DEFECTIVE INTERFERING PARTICLES AND USES THEREOF

This application claims benefit of provisional application Ser. No. 60/026,313, filed Sep. 18, 1996

BACKGROUND OF THE INVENTION

1. Field of the Invention

The present invention relates generally to the fields of molecular virology and immunology. More specifically, the present invention relates to viral defective interfering particles and uses thereof.

2. Description of the Related Art

"Incomplete particles" were discovered by von Magnus in 1947 during successive undiluted passages of influenza viruses (von Magnus '47). In general, these incomplete particles contain less than a full-length genome and are replication-defective. They can be rescued by and interfere with the replication of homologous helper viruses.

To date, most defective interfering particles are discovered in laboratory settings (Holland et al., '87 & '91; Dimmock '96). It is not known if defective interfering particles could also exist in natural infection in humans. Furthermore, most defective interfering studies have demonstrated a correlation between genomic deletion and the defective interfering phenotype. Whether deletion is indeed the cause to the defective interfering phenomenon and whether the identified deletion alone is necessary and sufficient for the defective interfering behavior, have never been proven experimentally.

Another important characteristic of these incomplete particles is their ability to enrich their proportion of the total viral yield in mixed infection with wild type and incomplete viruses (Holland '87). Based on these properties, Huang and Baltimore defined these biologically active defective particles as defective interfering (DI) particles and the replication competent homologous virions as standard virus (Huang & Baltimore, '70). Defective interfering particles are wide-spread in many DNA and RNA viruses in bacteria, plants and animals (Holland, '87; Huang & Baltimore, '77). The biological significance of these defective interfering particles remains an important and intriguing issue in virology and evolutionary biology. Defective interfering particles may play a key role in disease progression of chronic infection.

Hepatitis B virus (HBV) is one of the most common infectious agents in humans (approximately 200 million chronic carriers of HBV worldwide) and chronic active hepatitis B infection leads to the development of cirrhosis and liver cancer (Shih et al, '96). HBV infection is the most common cause of death due to viral infections in humans and is behind only malaria as a cause of death from an infectious agent. Every newborn should be vaccinated against HBV. To date, there is no simple, specific and effective therapy for a deadly fulminant hepatitis B infection.

The molecular and cellular mechanism of chronicity and pathogenesis of HBV infection remains to be elucidated. HBV replication in various hepatoma cell lines in tissue culture does not exhibit any apparent cytopathic effect (Sureau et al., '87; Shih et al., '89). It is generally believed that hepatitis and liver damage are due to immune-mediated cytotoxicity (Milich '91; Chisari & Ferrari, '95). HBV core antigen (HBcAg or nucleocapsid protein) has been shown to be a major target of T cell immunity (Mondelli et al., '82, Vento et al., '85; Ferrari et al., '90; Tsai etal., '92).

Immune escape mutations are known to occur within the major histocompatibility complex (MHC) class I-restricted cytotoxic T lymphocyte (CTL) epitopes (Pircher et al., '90; Phillips et al., '91). Surprisingly, frequent missense mutations of HBcAg were found to coincide with mapped MHC class II-restricted T cell epitopes (Hosono et al., '95; Lee et al., '96; Bozkaya et al., '96). In addition to these missense mutations, a naturally occurring core antigen internal deletion (CID) was found to be geographically ubiquitous in 4 out of 4 asymptomatic HBV carriers (Okamoto et al., '87), 7 out of 11 chronic active hepatitis (Wakita et al., '91), 2 out of 10 hepatocellular carcinoma tissues (HCC) (Hosono et al, '95) and 6 out of 6 HBV-infected immunosuppressed transplantation patients (Gunther et al., '95). More often, these deletions were in-frame, occurring around HBcAg codon 80–130, and varying in size from 18 to 61 amino acids (approximately 10–33% of wild type HBcAg). The amino terminal moiety of HBcAg is responsible for the polymerization of nucleocapsid particles, while the arginine-rich carboxyl terminus of HBcAg is known to be involved in binding of HBV pregenomic RNA and the reverse-transcribed cDNA(Gallina et al., '89; Hatton et al., '92). The internal deletion of HBcAg is located outside the nucleic acid binding domain and its biological functions have been unclear.

Hepatitis B virus was discovered by Blumberg in 1964 and the initial reports of core internal deletion (CID) mutants of HBV was by Okamoto et al. in 1987 and Wakita et al. in 1991. However, there has been no report of HBV defective interfering particles. Previously, Gerin et al. reported the identification of HBV defective interfering particles based on the morphology of "empty" particles under electron microscope. (*American J. of Path.,* 81:651–668, 1975). As mentioned earlier, the definition of defective interfering is a functional one, not strutural. Morphological features are neither a necessary nor a sufficient criterion for the definition of defective interfering particles. To the contrary, defective interfering particles are not "empty" or without viral genome. Defective interfering particles do have a functionally defective genome. Therefore, defective interfering particles are a life form which can perpetuate itself, while "empty" particles are not life form, since they are simply protein aggregates and do not have a genome to duplicate themselves. Although there has been speculation that CID mutants of HBV could be defective interfering particles (Akarca & Lok, '95), no experimental data, evidence and proof of the four major characteristic features of defective interfering particles, i.e., replication defective, rescuability by helper viruses, interference of helper virus, and enrichment of defective interfering particles, has been reported. As admitted by the authors, "We acknowledge that we do not have direct proof that the deletions result in defective genomes" (p. 1825 near the end, Akarca & Lok, '95). This deficiency in the prior art's ability to determine defective interfering particles is in part due to both technical and conceptual difficulties.

The conventional approach of identifying defective interfering particles relies on plaque assay and infection assay. Since HBV infection in tissue culture is not a well established procedure, and HBV replication in tissue culture does not produce plaques, there is no prior art as to how to determine the presence of defective interfering particles without infection and plaque assay. The CID mutants also contain a number of mutations elsewhere in the HBV genome. It is not obvious how one could circumvent these complications to study the native naturally occurring CID mutation without the enormous complication from other coexisting mutations in the CID variants.

A misconceptual difficulty in the prior art involves the nomenclature of defective interfering particles. In fact, "enrichment" is another equally important feature of defective interfering viruses. The prior art nomenclature often leads to the misconception that the overall viral titer will be dramatically decreased due to a dominant negative effect of defective interfering particles.

Laboratory-derived defective interfering particles of human hepatitis A virus (HAV) have been reported (Siegl et al., '90 and '93). However, these HAV-defective interfering viruses were originated from tissue culture in the laboratory setting. As admitted by the authors (Siegl et al., '90, page 106): " . . . Under conditions of natural infection, however, defective interfering particles of the very same viruses have not yet been observed. Hence, it is not known whether the predicted positive and/or negative effects of this specific class of particles play the expected role during natural infection . . . ". Second, HAV and HBV are different viruses. HAV is an RNA virus transmitted via the oral-fecal route while HBV is a DNA virus transmitted through blood and intimate contact.

The prior art is deficient in the lack of the understanding, experimental support, evidence and proof of the functional behaviors of defective interfering particles in human viruses in natural infections. The present invention fulfills this longstanding need and desire in the art by providing experimental data, evidence and proof of the functional features of human defective interfering viruses.

SUMMARY OF THE INVENTION

Internal deletion of human hepatitis B virus (HBV) core antigen is frequently found in HBV infections worldwide. Functional characterization of these mutants revealed features reminiscent of defective interfering particles (DI) originally discovered in influenza virus half a century ago. Internal deletion of HBV core antigen is necessary and sufficient for the defective interfering phenotype. The virus-virus interactions between the populations of wild type and defective interfering particles could provide a way of quantitative modulation of immune targets in virus-host interactions in pathogenesis and persistence of HBV infection. The present invention demonstrates the first experimental evidence that defective interfering variants exist in natural infection in humans. The present invention also determined whether the naturally occurring CID mutation, identified from HBV-infected human patients, can confer any defective interfering phenotype when this mutation is introduced into a wild type HBV background.

In one embodiment of the present invention, there is provided a composition of matter comprising a defective interfering virus particle, wherein said particle naturally occurs in a human infection and wherein said particles has a naturally occurring core antigen internal deletion.

In another embodiment of the present invention, there is provided a pharmaceutical composition, comprising defective interfering virus particle and a pharmaceutically acceptable carrier.

In yet another embodiment of the present invention, there is provided a method for preparing defective interfering virus, comprising the steps of: (1) introducing a defective interfering virus and a complementing plasmid expressing a wild type virus core antigen and optionally containing a drug resistance gene, into a recipient cell; (2) selecting for stably transfected colonies; (3) growing the drug resistant cells and screening for the production of virus DNA replication; and (4) collecting defective interfering virus particles from the medium.

In still yet another embodiment of the present invention, there is provided a vaccine, comprising a defective interfering virus particle of the present invention.

In yet another embodiment of the present invention, there is provided a vector comprising a DNA sequence coding for a defective interfering virus particle of the present invention, wherein the vector is capable of replication in a host and said vector comprises, in operable linkage: a) an origin of replication; b) a promoter; and c) a DNA sequence coding for a defective interfering virus particle.

In yet another embodiment of the present invention, there is provided a host cell transfected with a vector of the present invention, said vector expressing a defective interfering virus particle of the present invention.

In yet another embodiment of the present invention, there is provided a novel cell line producing the defective interfering virus particle of the present invention.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1 shows that the HBV-CID variants are replication defective upon transfection into human hepatoma cell line Huh7. FIG. 1A illustrates the deletion regions of HBV core antigen of two different CID variants identified from two different hepatoma patients T85 and T109. This deletion region does not overlap with any other HBV genes, including X, P (polymerase) and pre-S/S (envelope). DEL85 deleted amino acids 88–135 while DEL109 deleted amino acids 82–122. To construct plasmids pDEL85 and pDEL109, the DNA fragments of nucleotide 1636 to 2688 containing the mutant HBV core gene were PCR amplified from total DNA samples of hepatomas T85 and T109 (Hosono et al., '95), and were used to replace both copies of the wild-type counterparts of an HBV tandem dimer plasmid (Roychoudhury & Shih, '91). FIG. 1B shows that five days after transfection with wild type or mutant HBV, viral DNAs of intracellular core particles were harvested and subjected to Southern blot analysis using the 3.1 kb full-length vector-free HBV DNA probe (Yuan et al, '95). No detectable replication of mutants pDEL85 and pDEL109 were observed. FIG. 1C shows that encapsidation activity was assayed by primer extension using core particle-associated viral RNA from transfected culture and a 5'-end-labeled oligonucleotide primer (nucleotides 1980 to 2001) (Roychoudhury et al., '91). FIG. 1D shows that similar levels of the pregenomic RNA were produced from wild type and CID mutants. Twenty five micrograms of cellular RNA from transfected cells were subjected to Northern blot analysis and probed with a 3.1 kb full-length HBV probe (top). Similar amounts of cellular RNA were used in each lane as indicated by similar intensity of ethidium bromide staining (bottom). FIG. 1E shows that the reporter gene of chloramphenicol acetyl transferase (CAT) gene was fused in-frame with the carboxyl termini of the pol genes originated from pWT, pDEL85, and pDEL109. CAT activities of the pol-CAT fusion proteins were measured two days after transfection (Pei & Shih, '91). FIG. 1F shows that the core proteins produced from pWT, pDEL85, and pDEL109 were analyzed by immunoblot assay using a rabbit polyclonal anti-core antibody (Lanford).

FIG. 2 shows that the replication defective CID mutants can be rescued by trans-complementation with wild-type HBV core antigen and secreted into media with a similar buoyant density to wild-type HBV. FIG. 2A shows that various doses of a wild-type HBcAg expression vector, pSVC, was co-transfected with constant amount of pWT, pDEL85 and pDEL109, respectively. Viral DNAs of intracellular core particles were analyzed by Southern blot using the 3.1 kb full-length HBV probe. FIG. 2B shows that ten micrograms of pDEL85 or pDEL109 was either transfected alone or with 10 µg of pSVC. Extracellular HBV particles from 20 ml conditioned media were collected 5 days after transfection via centrifugation through a 20% sucrose cushion. FIG. 2C: medium collected from cells transfected with 10 µg of pWT. Viral particles in the media were purified and subjected to isopycnic centrifugation. Fractions were assayed for HBsAg using Abbott Auszyme EIA kit (top). Southern analysis located the fractions containing HBV genomes(bottom). FIG. 2D shows the medium from cells transfected with 10 µg of DEL85 and pSVC was assayed.

FIG. 3 shows the defective interfering phenomenon of HBV-CID variants were observed in human hepatoma Huh7 and HepG2 (FIG. 3D) cells. FIG. 3A shows that seven µg of pWT was co-transfected with increasing amounts of pDEL85, pDEL109, or pTGAGC, respectively. HBV core particle associated DNA was analyzed by Southern blot using 3.1 kb full-length HBV fragment. Replicative intermediates of relaxed-circular (RC) and single-stranded (SS) DNAs are indicated by arrows. FIG. 3B shows that after the 3.1 kb full-length HBV probe was removed from the nitrocellulose filter, the same filter was reprobed with a radiolabelled wild-type specific DNA fragment. The wild-type specific DNA fragment is 135 nucleotides in length (from nucleotide 2141 to 2275) and was amplified by PCR using pWT as a DNA template. The relative intensity of replicative intermediates was measured by densitometer image analysis. FIG. 3C: after the wild-type specific probe was removed, the nitrocellulose filter of FIG. 3B was reprobed with DEL85-specific and DEL109-specific fragments. The DEL85 specific DNA probe is 181 nucleotides (from nucleotide 2041 to nucleotide 2365 with a deletion of 144 nucleotides) and synthesized by PCR using pDEL85 as a DNA template. The DEL109 specific probe is 208 nucleotides (from nucleotide 2041 to 2365 with a deletion of 123 nucleotides) and synthesized by PCR using pDEL109 as a DNA template. The non-specific hybridization of background noise around SS DNA region was observed in lanes transfected with pWT alone or cotransfected with pTGAGC. FIG. 3D shows that the HepG2 human hepatoblastoma cell. line was used in the same assay with a wild type-specific probe. FIGS. 3E and 3F shows that the defective interfering phenomenon was also observed when the secreted extracellular HBV particles were analyzed in the replication assay using a full-length 3.1 kb HBV probe (FIG. 3E) and the wild type-specific probe (FIG. 3F). FIG. 3G shows a cartoon illustration of the wild type-specific and DEL- specific probes used above.

FIG. 4 shows the comparison of the relative abundance of wild type and CID mutants via PCR analysis using HBV core gene-specific primers (16). Top, An aliquot of the premixed donor plasmid DNAs (pWT and pDEL85) was amplified by PCR before transfection. The results for pWT and pDEL109 (data not shown) are very similar to that of pWT and pDEL85. Bottom, seven µg of pWT were cotransfected with increasing amounts of pDEL85 (right) or pDEL109 (left) into Huh7 cells, and core particle-associated DNAs were harvested 5 days after transfection. Identical PCR conditions were used for both amplifications of the plasmid and core particle-associated DNAs. The relative intensities of full-length and deleted core gene fragments were measured by densitometric scanning.

FIG. 5 shows that the defective interfering phenomenon conferred by CID variants is species specific and not mediated through soluble factors. FIG. 5A shows the conditioned media of Huh7 cells were collected 2 days after transfection with various combinations of plasmids pWT, PSVC, and pDEL85. Huh7 cells transfected with 7 µg of pWT were then incubated with 5 ml of each respective conditioned media and 5 ml of fresh media. As a control, transfected culture incubated with 10 ml of fresh media were included in the last lane. Full-length 3.1 kb HBV DNA was used as a probe in replication assay. FIG. 5B shows that seven micrograms of duck hepatitis B virus plasmid (pSP65DHBV5.1) was co-otransfected with increasing amount of pDEL85, pDEL109, or pTGAGC into Huh7 cells. Replication assay was performed as described in FIG. 1 above and probed with 3.1 kb full-length DHBV fragment.

FIG. 6 shows that the internally deleted core proteins can be detected in vitro but not in vivo. The flu-epitope peptide sequence (YPYDVPDYA) from the influenza hemagglutinin (Field et al., '88) was introduced into the carboxyl termini of the core proteins using an SV40 expression vector. The wild-type core protein from pWT, and the wild-type and deleted core-flu fusion proteins from pSVCflu, pSV85flu, and pSV109flu were measured by immunoblot assay using anti-core (FIG. 6A) or anti-hemagglutinin (FIG. 6B) antibody. FIG. 6C shows that the absence of the deleted core-flu fusion protein is not due to the instability of its mRNA. Twenty-five micrograms of cellular RNAs from cells transfected with either pSVCflu, pSV85flu, or pSV109flu were hybridized with wild-type-, DEL85-, and DEL109-specific RNA fragments respectively in the RNase protection assay. FIGS. 6D and 6E show that if the deleted core gene is indeed translatable, the wild-type and deleted core proteins were expressed in vitro from pSPC, pSP85, and pSP109 using rabbit reticulocyte lysate (Promega Co., Wis.). The in vitro synthesized proteins were analyzed on a 12% acrylamide gel either in the presense (FIG. 6D, top) or absence (FIG. 6E) of 2-mercaptoethanol. pSP109ATA is a similar plasmid to pSP109, except that the initiation codon ATG of the core gene has been changed to ATA. To control for the equal amount of RNAs used in the in vitro translation experiment described in FIG. 3D, the in vitro synthesized RNA transcripts from these plasmids were quantitated by electrophoresis (FIG. 6D, bottom). The β-actin transcript with a size of 360 nucleotide from pRT1 was used as positive control and size marker. FIG. 6F shows that no apparent interference effect on wild type HBV replication was observed by the deleted core protein from cotransfected pSV109 or pSV109ATA. The replication assay was performed as described using the 3.1 kb full-length HBV probe.

FIG. 7 shows the cycling-like phenomenon of HBV defective interfering mutants in the serially collected serum samples (1989–1993) from an HBV-infected patient with hepatocellular carcinoma. FIG. 7A shows that HBV DNA in the sera were prepared (Wakita et al., '91) and PCR amplified as detailed (Hosono et al., '95). Amplified DNA fragments were separated by agarose gel electrophoresis and stained with ethidium bromide. ALT (alanine amino transferase) has been used as a clinical indicator of liver damage. The normal upper limit of ALT activity is approximately 40 IU/liter. Acute hepatitis patients often have several hundred IU per liter. FIG. 7B shows the comparison of HBV core amino acid sequences among DEL85, wild type (consensus), and viruses serially collected from a chronic active hepatitis B patient (December 1989–December 1993). The consensus sequences used here are the most prevalent HBcAg sequences in Asia (Ono et al., '83; Kobayashi & Koike, '84). PCR amplified DNA fragments were gel-purified, subeloned and sequenced as described (Hosono et al., '95). The letter "Z" represents a translational stop codon and the letter "X" represents deletion. The symbol "/" represents frame shift mutation. Subtype specific sequence heterogeneity was indicated by *. Hotspot mutational domains I and V coincides with MHC class II-restricted T cell epitopes (Hosono et al., '95). Recent studies also indicated that domain IV contains an MHC class II-restricted T cell epitope (Jung et al., '95; Tsai et al., '96). The sequences of CID mutants are highlighted with yellow color. Frequent missense mutations at codons 13, 151, and 182 are present in helper virus and absent in defective interfering virus, and are highlighted with pink color. pol represents the overlapping polymerase gene. FIG. 7C shows the case F090245 from 1986 to 1991. Serum samples from 1987 and 1988 were not available. FIG. 7D shows the case F090063 from 1986 to 1991. Each sample was PCR-amplified, then gel analyzed in duplicate.

FIG. 8 shows that the same CID deletion as DEL85 was also observed in a British patient and a patient from Hongkong.

FIG. 9 shows that stable Q7 rat hepatoma cell lines were transfected with plasmids pSVC and pSV2NeoDEL85 and were selected with G418 as described previously. HBV core particle-associated DNA was purified from 6 independent clones and characterized by gel electrophoresis and Southern blot analysis. Two neomycin-resistant clones, 1-12-2 and 1-15-1, exhibited the pattern characteristic of HBV replication intermediates such as relaxed circular (RC) and single stranded forms of DNA.

DETAILED DESCRIPTION OF THE INVENTION

Definitions

Figure 1A:
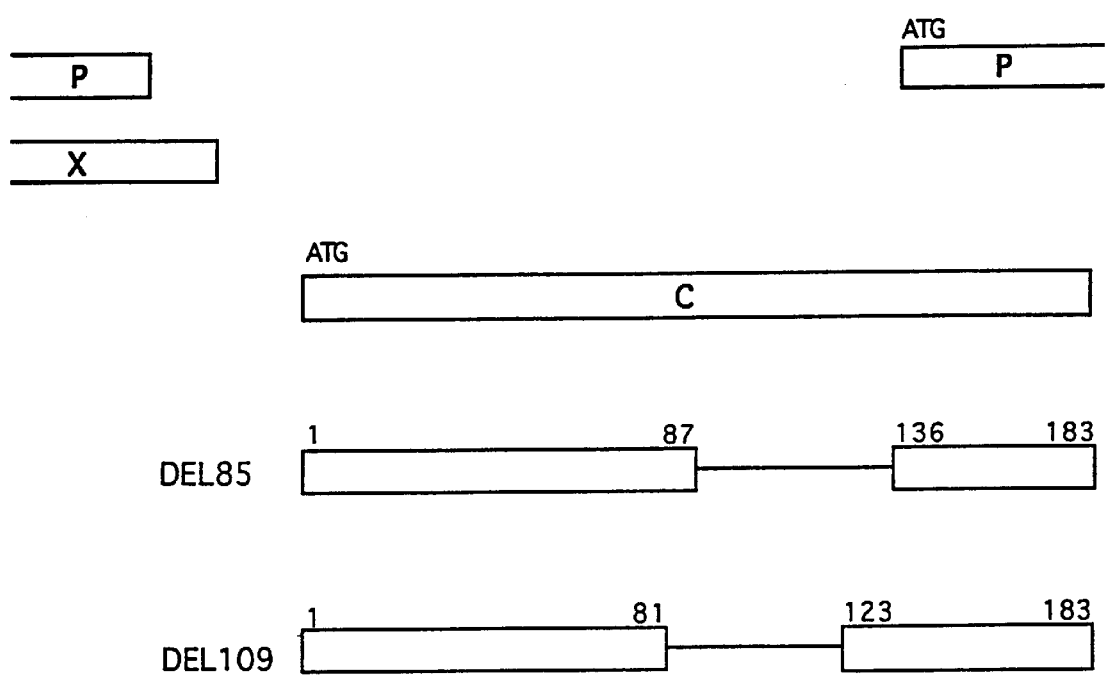
Figure 1B:
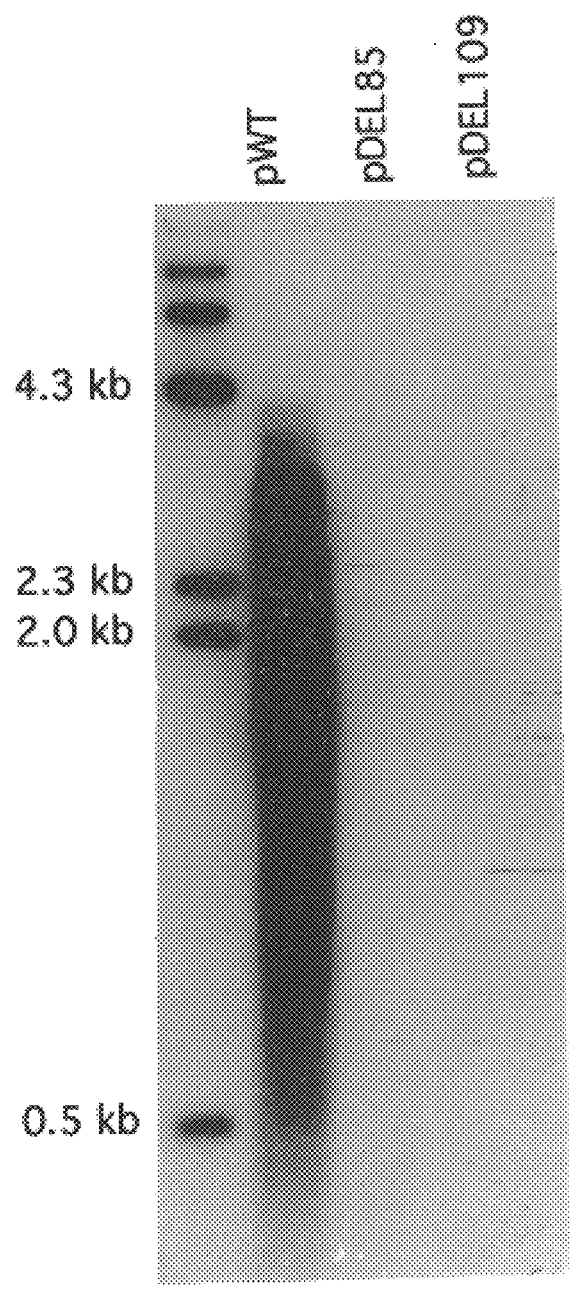
Figure 1C:
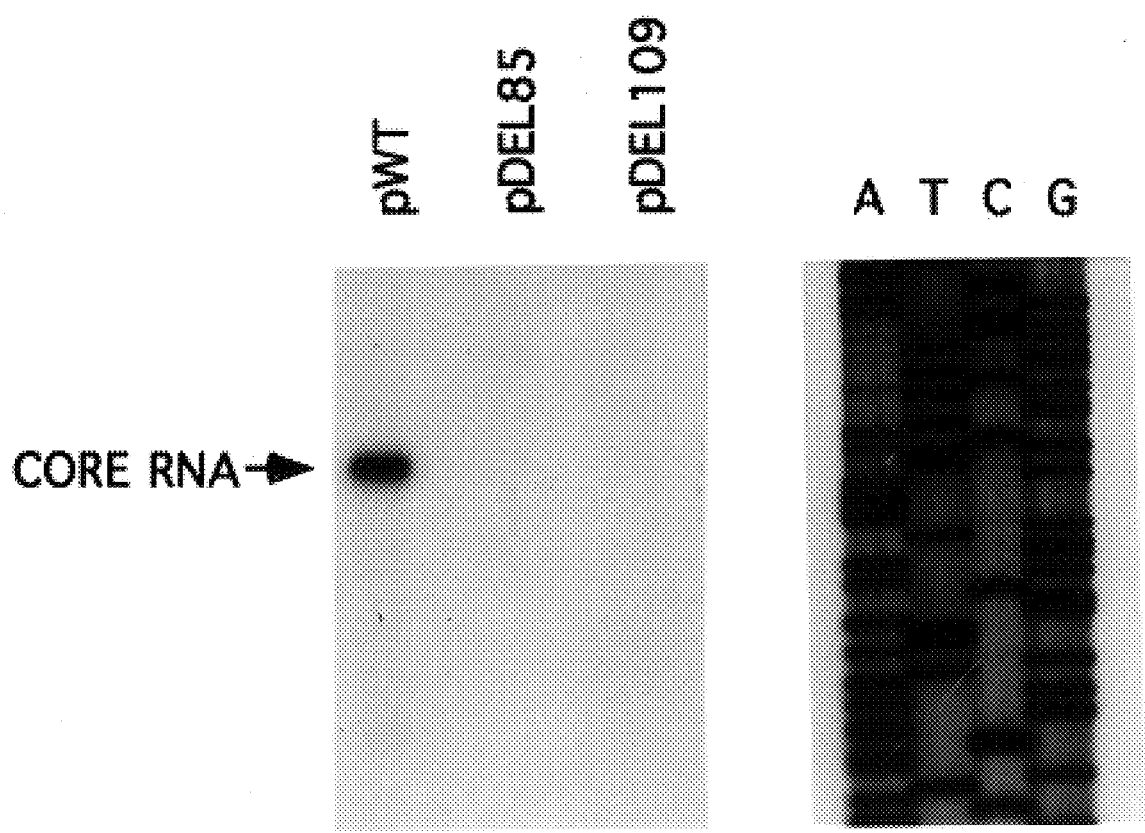
Figure 1D:
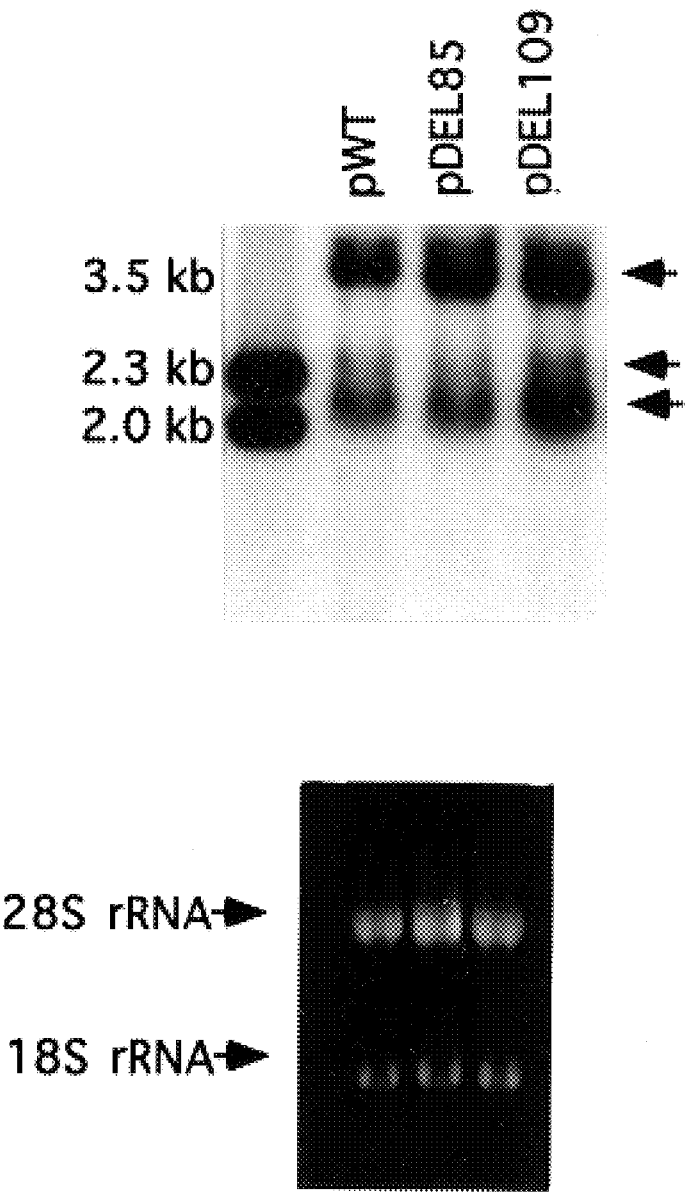
Figure 1E:
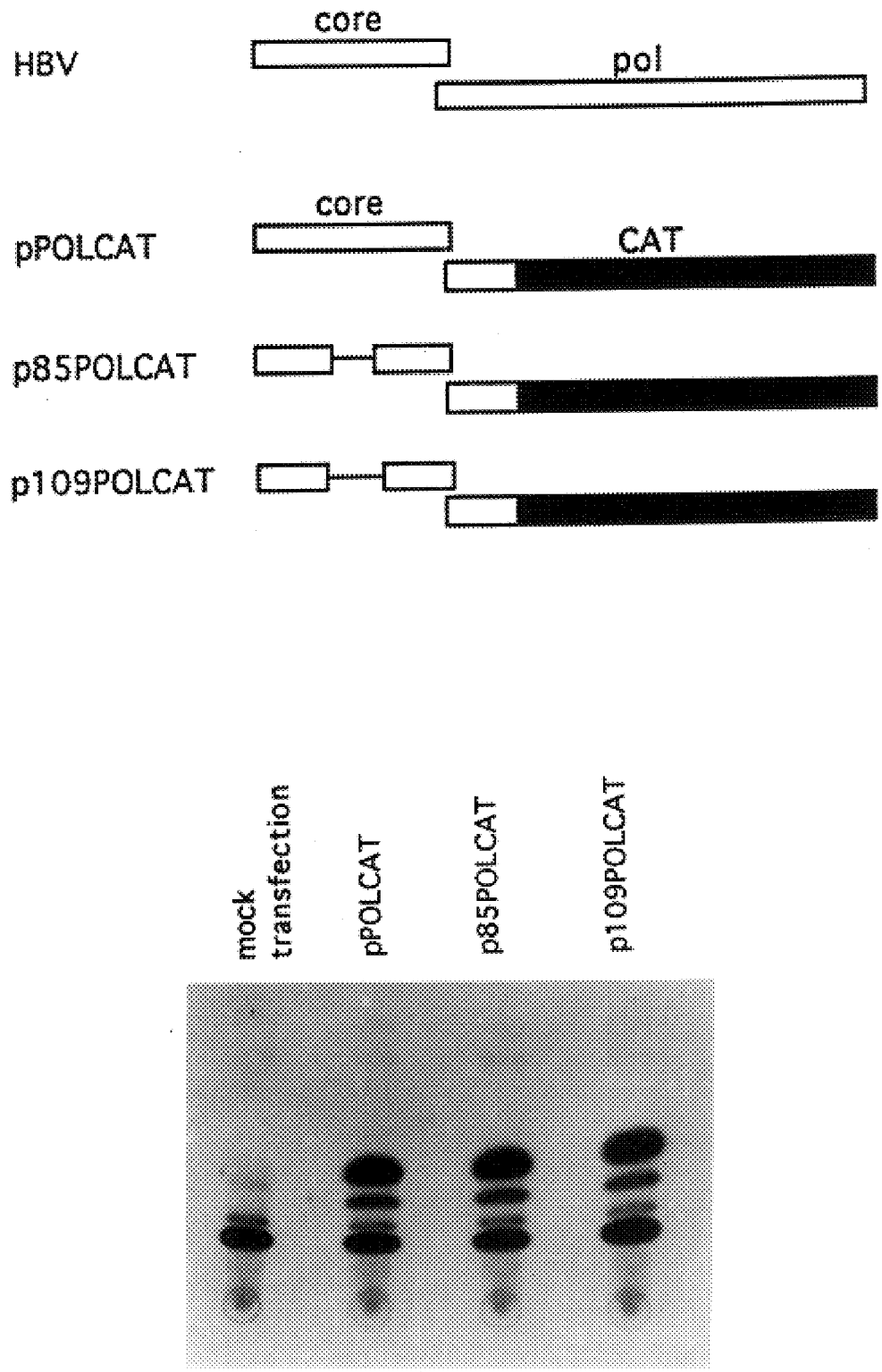

The following terms are defined as used herein. Terms not defined should be interpreted as is usual and customary in the fields of molecular biology and virology.

As used herein, the term "replicative defective" shall mean that a virus is unable to duplicate or multiply by itself.

As used herein, the term "interfere" shall mean a decrease in the number of helper viruses.

As used herein, the term "incomplete particle" shall refer to the virus variants that can interfere with the replication of other viruses.

As used herein, the term "defective interfering" shall refer to the fact that viral particles are replication defective, rescuable by helper viruses, have an interference effect on wild type virus, and enrich the replication defective virus.

As used herein, the term "immune escape mutation" shall mean a mutation which allows immune evasion from a host's immune surveilance.

As used herein, the term "trans complementation" shall mean a genetic experiment designed to determine if two different genetic entities, e.g., two different viruses or plasmids, could cross support each other.

As used herein, the term "cycling-like phenomenom" shall mean a dynamic equilibrium between the defective interfering particle and the helper viruses and describes the reciprocal relationship between the defective interfering and the helper viruses.

As used herein, the term "core antigen internal deletion" or "CID" shall mean a deletional mutation within the central portion of the HBV core antigen, e.g., around amino acids 80 to 130.

As used herein, the term "rescuability" shall mean the ability to survive when supplied with the normal functional core proteins.

As used herein, the term "enrichment" shall mean to increase in proportion in a mixture of different viruses.

As used herein, the term "hotspot" or a "hotspot mutation" shall mean a highly frequent mutation.

As used herein, the term "immunologically anergic" shall mean unable to induce an immune response.

As used herein, the term "immunogenic agent" refers to an agent used to stimulate the immune system of a living organism, so that one or more functions of the immune system increased and is directed towards the immunogenic agent. Immunogenic agents include vaccines. Immunogenic agents can be used in the production of antibodies, both isolated polyclonal and monoclonal antibodies using techniques well known to those of ordinary skill in this art.

As used herein, the term "vaccine" is meant an agent Aused to stimulate the immune system of a living organism so that protection against future harm is provided. Immunization refers to the process of inducing a continuing high level of antibody against cellular immune response in which T-lymphocytes can either kill the pathogen and/or activate other cells, e.g., phagocytes to do so in an organism, which is directed against a pathogen or antigen to which the antigen has been previously exposed.

As used herein, the term "individual" is meant any member of the subphylum Vertebrata. All vertebrates are basically capable of responding to vaccines and producing antibodies.

Although vaccines are commonly given to mammals, e.g., humans and dogs, vaccines for commercially raised vertebrates of other classes may be within the scope of the present invention.

Vaccination

An "effective amount" of live-virus or subunit vaccine prepared as disclosed herein can be administered to a subject (human or animal) alone or in conjunction with an adjuvant (e.g. as described in U.S. Pat. No. 5,223,254 or Stott et al., (1984) *J. Hyg. Camb.* 251–261) to induce an active immunization against a pathogenic infection. An effective amount is an amount sufficient to confer immunity against the pathogen and can be determined by one of skill in the art using no more than routine experimentation.

Determination of an effective amount may take into account such factors as the weight and/or age of the subject and the selected route for administration. Vaccines can be administered by a variety of methods known in the art. Exemplary modes include oral (e.g. via aerosol), intradermal, intramuscular, intraperitoneal, intravenous, subcutaneous, parental, transdermal and intranasal routes. If necessitated by a particular mode, the vaccine may be encapsulated.

Current commercial HBV vaccine consists of HBV-encoded envelope protein alone. It does not have other HBV-encoded protein antigens, such as polymerase, preS1, preS2 or core antigen (also known as nucleocapsid antigen). Pre-S1 antigen is present in HBV virion and effective in protection (Milich et al., '85; Neurath et al., '85 & '88). In addition, the HBV-defective interfering vaccine should be virtually identical in every aspect to the fully infectious HBV in nature, except that HBV-defective interfering mutant is not viable and not infectious. Thus, the HBV-defective interfering vaccine of the present invention will produce a much stronger, more effective, and long-lasting protection against HBV infection than the current surface antigen subunit vaccine. The HBV-defective interfering vaccine failure rate would also be much lower.

The HBV-defective interfering vaccine of the present invention may not be suitable for a small fraction of babies born to HBV carrier mothers, i.e., babies preinfected with HBV in utero or perinatally infected with HBV during delivery before vaccination. In both cases, the conventional subunit vaccine could not be effective either. The HBV-defective interfering vaccine of the present invention is most safe for babies born to healthy noncarrier mothers, who are the majority (>80 or 90%) of the pregnant population. One specific application of the HBV-defective interfering vaccine of the present invention is to use an active-passive immunization protocol (Beasley et al., '83). That is, one would administer to the newborns both HBIG (hepatitis B immunoglobulin) and the HBV-defective interfering vaccine of the present invention, instead of conventional subunit vaccine, within the first two hours after delivery.

The art of vaccine production and delivery is well established. A person having ordinary skill in this art would be able to use the defective interfering particles of the present invention in a vaccine and determine the appropriate dosages without undue experimentation. One possible regimen for vaccination would be: 2–3 doses of alum-absorbed defective interfering particles 5 μg/ml are injected intramuscularly. The defective interfering virus can be prepared from a tissue culture medium of a stable hepatoma cell line producing and secreting defective interfering, e.g., HBV defective interfering particles.

Figure 3A:
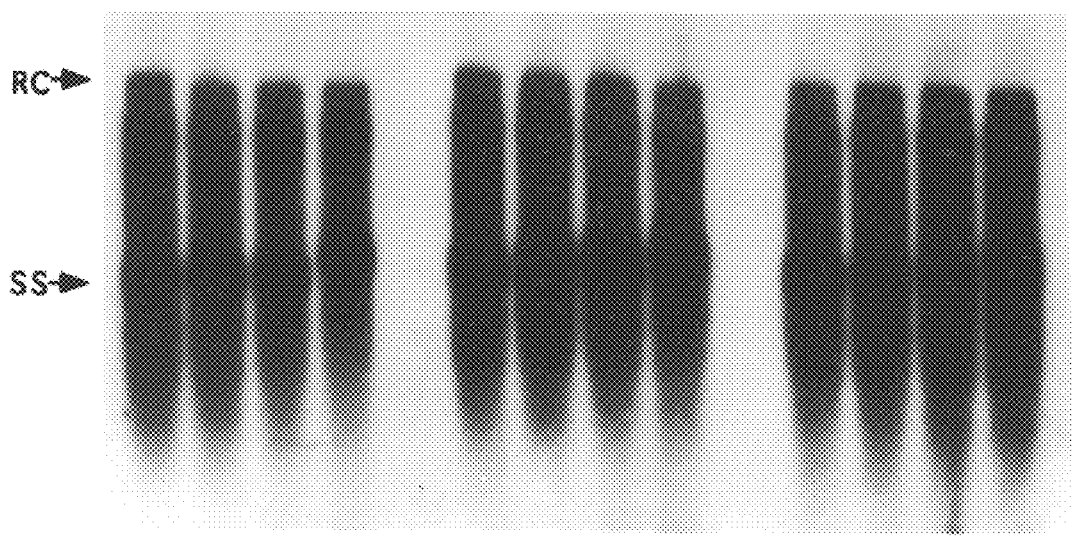
Figure 3B:
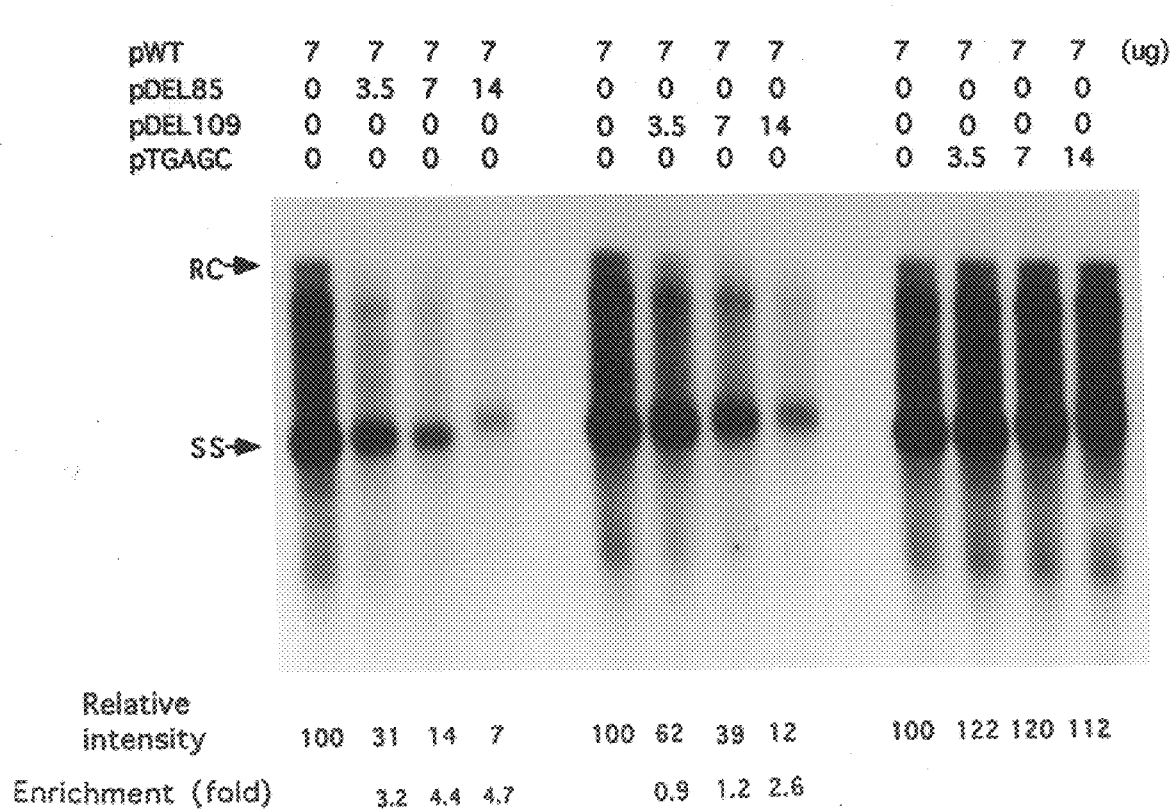
Figure 3C:
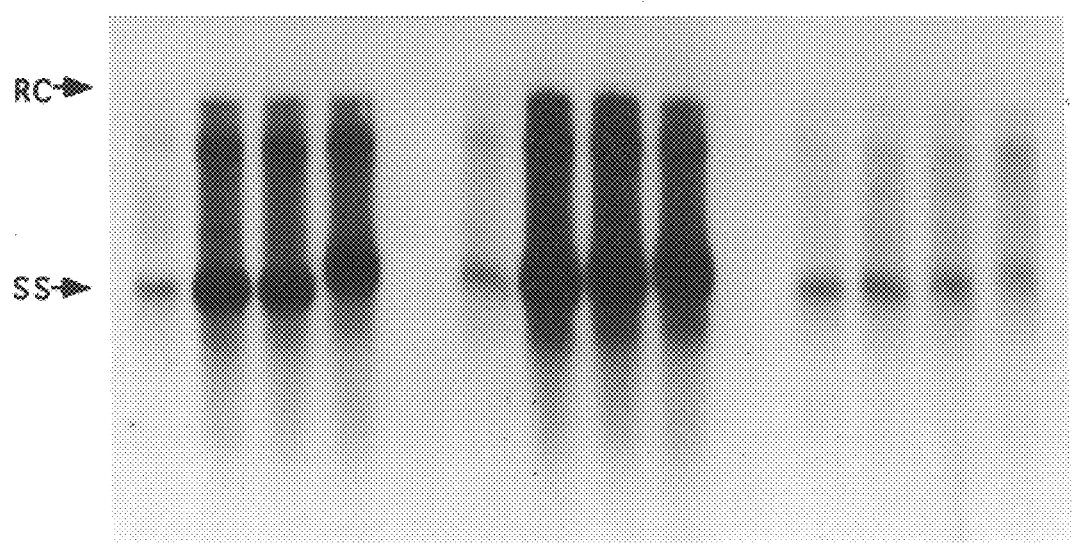
Figure 3D:
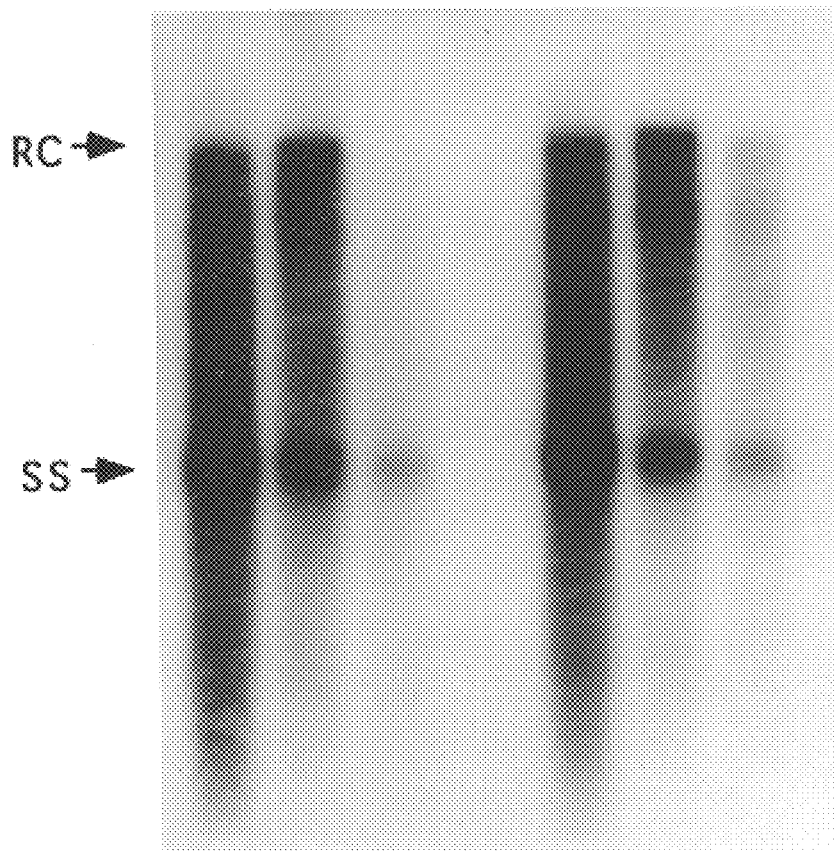
Figure 3E:
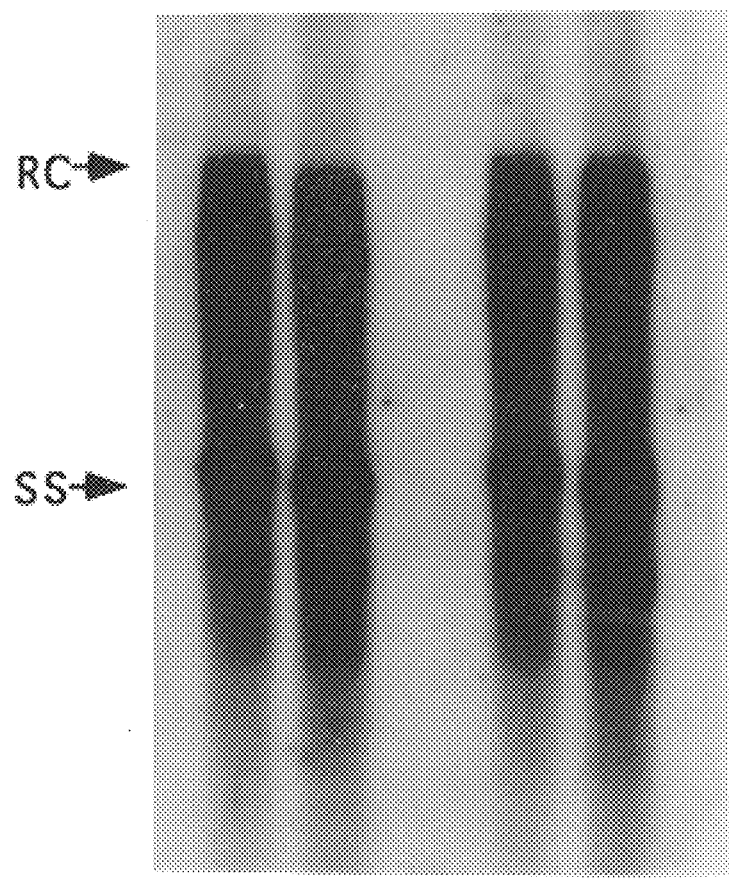
Figure 3F:
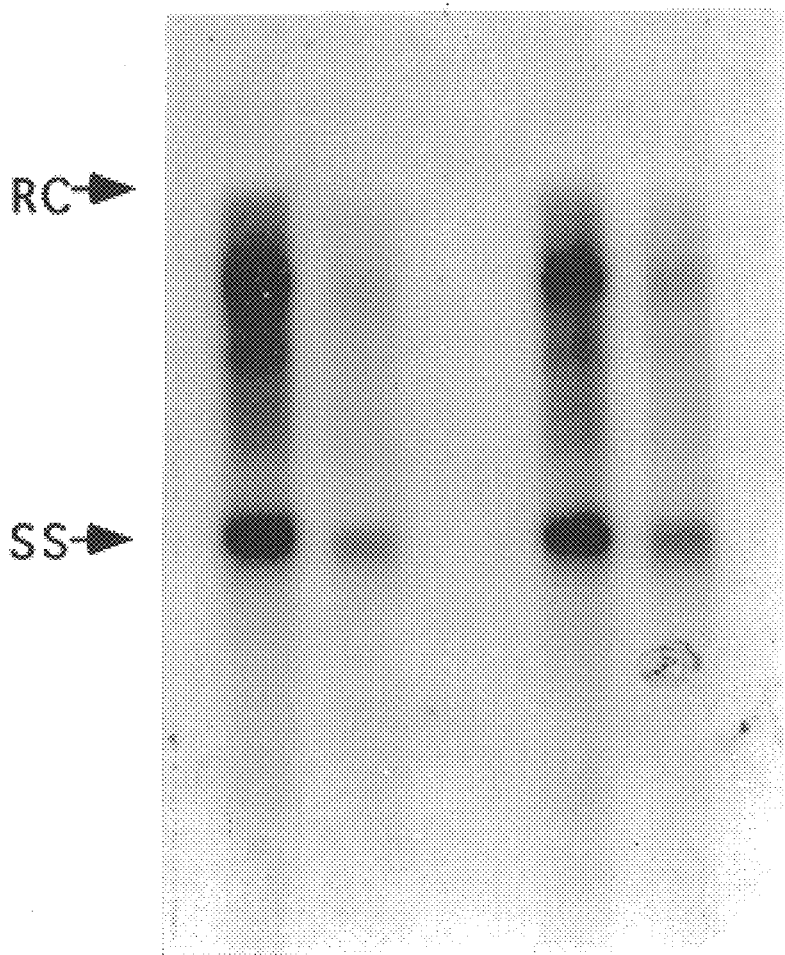
Figures 1, 3G:
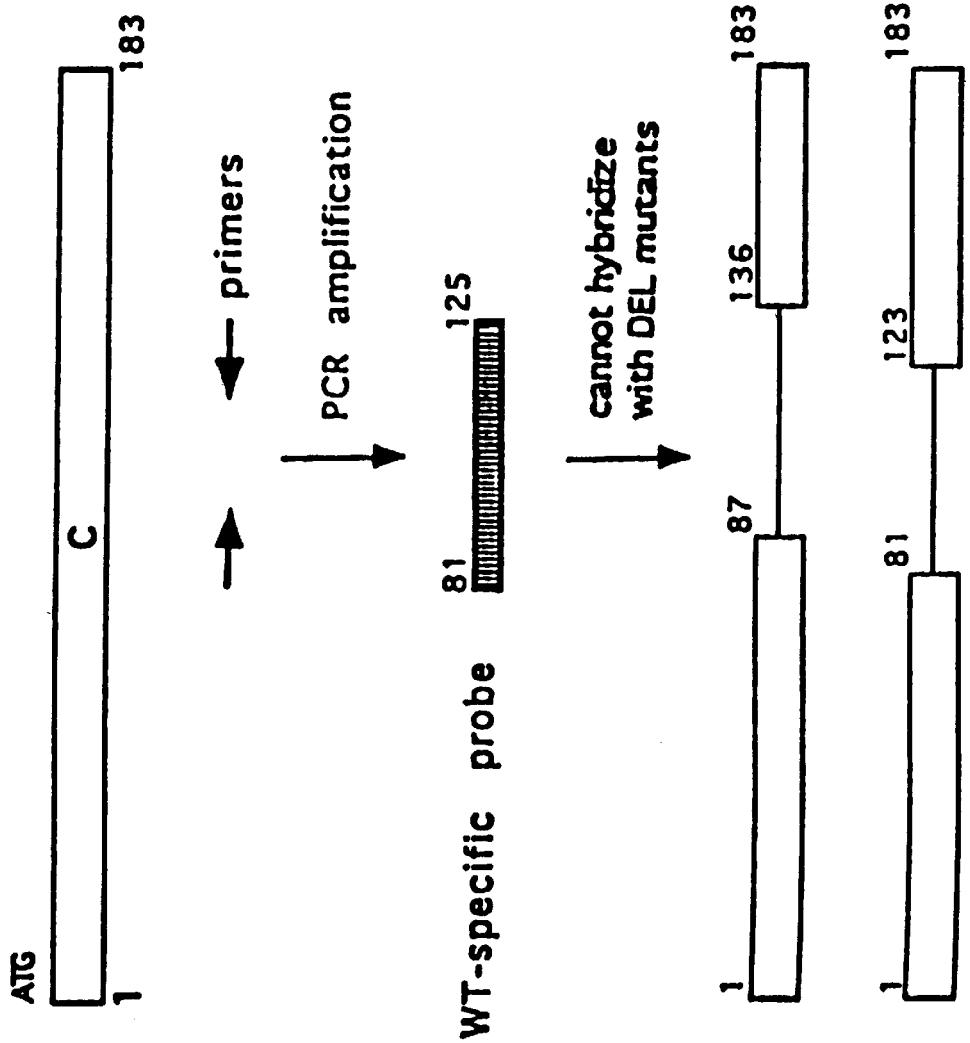
Figures 2, 3G:
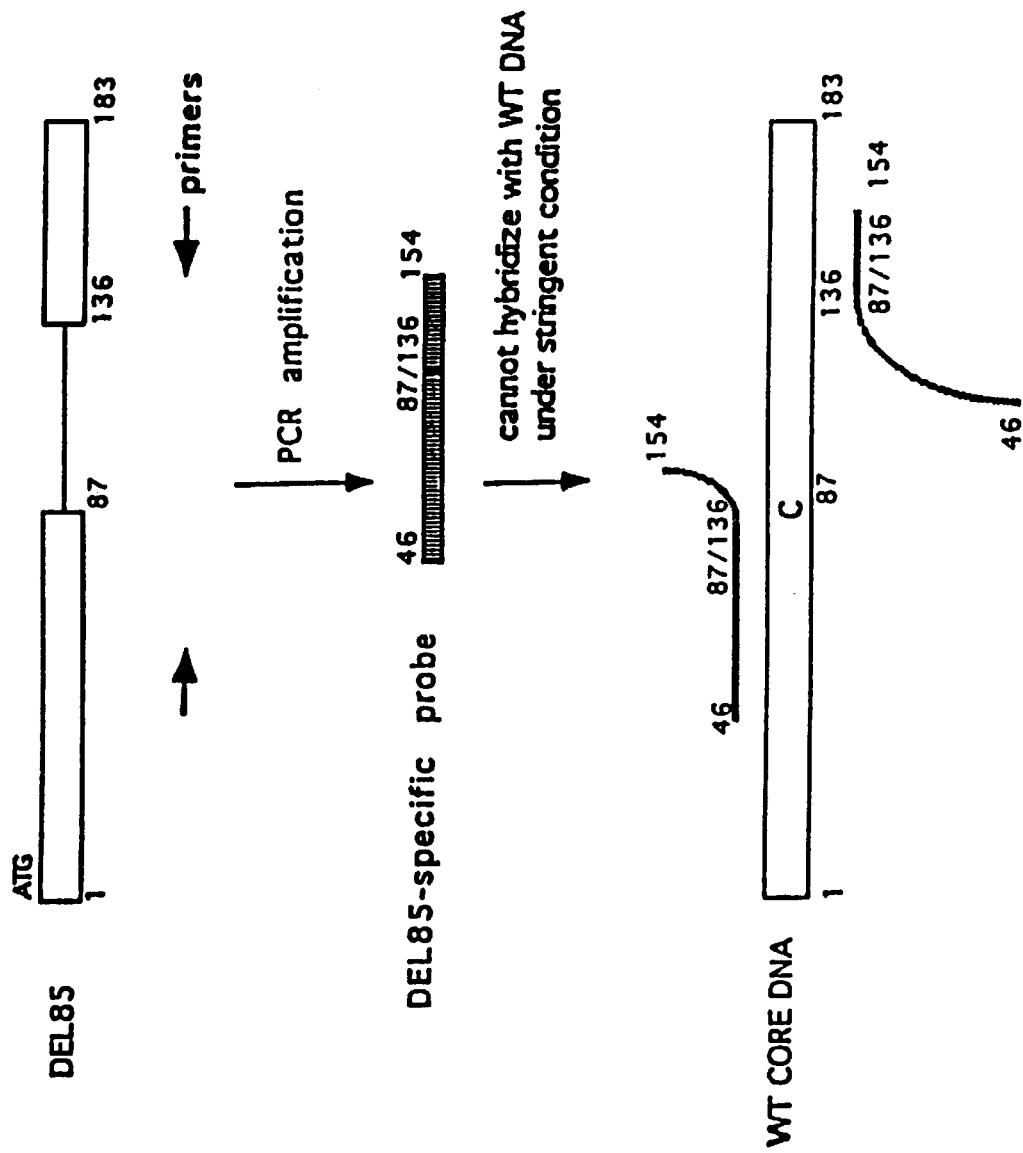
Figure 4:
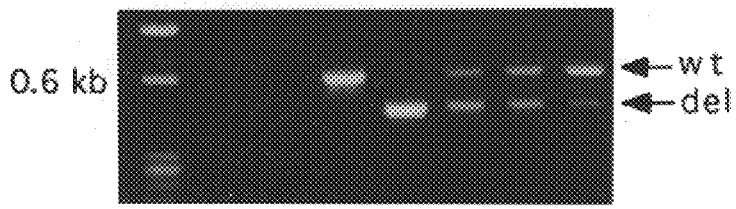
Figure 4:
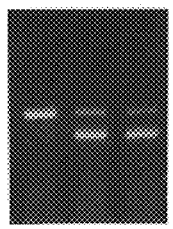
Figure 4:
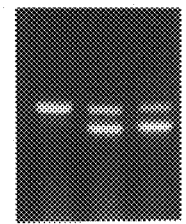

The procedure for preparing defective interfering viruses are detailed below as an example and the methodology is further described in Shih et al., '89; U.S. Pat. No. 5,156,970. These steps include (1) Introduce both defective interfering viruses, e.g., HBV-DEL85 and the complementing plasmid, e.g., pSVC which expresses the wild type HBV core antigen, into the same recipient cell (e.g., HepG2, Huh7 or Morris hepatoma 7777 cell lines) via a gene transfer techniques, e.g., calcium phosphate transfection technique, lipofectin technique. Ideally, but not necessarily, one of these plasmids contains a drug resistance gene, e.g., neomycin resistance. (2) Select for the stably transfected colonies using a medium containing selective drugs, e.g., neomycin resistance. (3) Grow up these drug resistant cells and screen for the production of HBV surface antigen and core/e antigen in the medium via enzyme immunoassay, e.g., Abbott EIA kit. (4) Cell lines which can produce both surface and core/e antigen are screened for HBV DNA replication using Southern blot analysis and the full length HBV DNA probe. HBV DNA is isolated from the intracellular core particles (for further details, see Examples 3 and 5 below). (5) Confirm the above Southern results using a defective interfering virus-specific probe, e.g., DEL85 mutant specific probe described in Example 14 and FIG. 3C. (6) Screen for the cell lines that produce the most abundant quantity of defective interfering viruses as in steps 4 and 5 described above. Test the genetic stability of the chosen cell lines by comparing the replication activities of cells in the presence or absence of the selective drug in the medium for a certain period (e.g., one month). Alternatively, genetically stable DI virus-producer cell lines can be further adapted or selected for growth in medilim of lower cost, such as lower concentration of fetal bovine serum, or calf serum instead of fetal calf serum. Selected clones can also be adapted to grow in suspension, instead of adhering to the surface of the culture container. Store such high-producer cell lines in Dulbecco Modified Eagle's Medium (DMEM) containing 10% fetal bovine serum (FBS). Long term storage of these cell lines can be made using DMEM containing 10% fetal bovine serum and cryopreseravatives, e.g., 10% glycerol or 10% DMSO, in liquid nitrogen. Reactivation of these cell lines can be done quickly by thawing the frozen vials at 37° C. in a water bath and gradually diluting the cell culture to a 10 fold final volume using DMEM with 10% FBS. Once the most ideal cell clones have been selected (i.e., highest yield of DI virus production, genetically stable, grow well in inexpensive medium, adapted for scale-up production, and other desirable features), they can be expanded in cell number and aliquoted to a number of frozen vials (e.g., 100 vials). These are referred to as cells of early passages. Cells from the early passages can be again expanded and aliquoted into a large number of vials, referred to as cells of late passages. When cells of late passages are no longer available (e.g., due to the loss of rulture by microbial contamination or inadequate culture condition), cells from early passage will be used to create more frozen cells of late passage. This is the so-called seed-lot system commonly used for manufacturing biological products. The method for the scale up production of DI virus will be the same as the routine scale up production of mammalian cells. (7) Defective interfering virus particles are collected from the medium (See Example 4). (8) The defective interfering virus pellets are resuspended in phosphate buffered saline (PBS). To clean up the virus preparation further, one can dialyze against PBS at 4° C. overnight or repeat the centrifugation and resuspension steps. (9) The defective interfering virus preparation can be stored in 10% glycerol or DMSO in PBS at −70° C. or a lower temperature. These virus preparations, after reactivation at room temperature are used for vaccination or therapeutic purpose. (10) The virus preparations obtained can be characterized further, such as by morphological examination via electron microscope or density gradient analysis. Further modification of the virus preparation for practical applications, such as vaccination, therapy and storage can be made. For example, aluminum-absorbed virus preparation can be used.

Therapy

An "effective amount" of an antiviral defective interfering particle of the present invention as a drug specifically interfering with the replication or transcription of a non-segmented virus, can be administered to a subject (human or animal). An effective amount is an amount sufficient to alleviate or eliminate the symptoms associated with viral infection. The effective amount for a particular antiviral agent can be determined by one of skill in the art using no more than routine experimentation. Determination of an effective amount may take into account such factors as the weight and/or age of the subject and the selected route for administration.

Antiviral agents can be administered by a variety of methods known in the art. Exemplary modes include oral (e.g. via aerosol), intradermal, intramuscular, intraperitoneal, intravenous, subcutaneous, parental, transdermal and intranasal routes. If necessitated by a particular mode, the gene therapy vector may be encapsulated.

It is specifically contemplated that pharmaceutical compositions may be prepared using the novel HBV-defective interfering particles of the present invention. In such a case, the pharmaceutical composition comprises the novel HBV-defective interfering particles of the present invention and a pharmaceutically acceptable carrier. A person having ordinary skill in this art would readily be able to determine, without undue experimentation, the appropriate dosages and routes of administration of the novel HBV-defective interfering particles of the present invention. Application of HBV-defective interfering particles of the present invention could be used to treat acute hepatitis patients (fulminant hepatitis). These patients have extremely high mortality rate (60–90%) within a very short period (a few days to 2 weeks). There is no effective treatment currently available for fulminant hepatitis.

Treatment of patients with deadly fulminant hepatitis with the HBV-defective interfering particles of the present invention may convert some patients to chronic asymptomatic carriers or chronic active hepatitis. If a patient is converted to chronic asymptomatic carriers, no further treatment of these healthy carriers is necessary. If a patient is converted to chronic active hepatitis, intervention of chronic infection via further treatment, such as interferon-alpha, can be considered. In either case, the patient's life expectancy may be prolonged by decades.

In the therapy of patients with deadly fulminant hepatitis with the HBV-defective interfering particles of the present invention, a person having ordinary skill in this art could determine the dosage needed with routine experimentation. Most likely, higher titer of defective interfering particles (such as $10^8$ or $10^9$ particles in a few c.c. in one shot per patient) will be most effective. The defective interfering virus can be stored in 10% glycerol or DMSO in PBS at a very low temperature. Before injection, the frozen vials of defective interfering viruses can be thawed at room temperature. Intravenous injection may be an optimal route of administration.

Therapy using these HBV-defective interfering particles is not limited to fulminant hepatitis patients; this therapy is useful to treat chronic or acute hepatitis. As long as the titer of the wild type HBV is significantly reduced by the defective interfering viruses, the hosts' immune system will do the rest.

The present invention discloses the presence of defective interfering viruses in humans, which will not be limited to HBV. Two indepentently derived HBV-CID mutants (pDEL85 and pDEL 109) isolated from two different patients (T85 and T109) are the first proof of human defective interfering viruses in natural infections. Thus, the present invention is directed to HBV-defective interfering particles. In addition, HBV defective interfering mutants containing a genetic defect, e.g., a missense mutation or out of frame deletion, in any part of the HBV genome, within or outside the nucleocapsid protein, is also within the scope of the present invention.

The present invention demonstrates the existence of naturally occurring CID mutants that are defective interfering-like particles. However, it is possible that defective interfering particles of HBV or other viruses can be created, e.g., by site-directed mutagenesis. Using such techniques, a person having ordinary skill in this art would be able to prepare or create other human defective interfering viruses or other human defective interfering-HBV viruses having different structural lesions.

Although the infectivity of DEL85 and DEL109 defective interfering-HBV has not been shown directly, a person having ordinary skill in this art would interpret the following data as evidence of their infectivity. First, the protein moiety of these HBV-defective interfering particles, including envelope, core, polymerase and X proteins, is bascially identical to wild type HBV. Further, the deleted core protein is extremely unstable in vivo. Therefore, the nucleocapsid of the defective interfering-HBV is probably made up exclusively from wild type core protein. Second, when the secreted defective interfering-HBV particles were banded on gradient centrifugation, their sedimentation profile was indistinguishable from that of wild type HBV. Wild type HBV produced in tissue culture in this way was infectious (e.g., Shih et al., '89).

In one specific embodiment of the present invention, a novel stable cell line is provided. HBV-defective interfering particles can be rescued by supplying the wild type core protein in a co-transfection assay (FIG. 2). Thus, one can establish a stable cell line by introducing both an HBV-defective interfering plasmid and an expression vector of wild type core protein into the same replication permissive cells, such as the rodent Morris hepatoma cell line (Shih et al., '89) or human hepatoma cell line HepG2 as is well known to those having ordinary skill in this art.

Replication permissive cell lines are not limited to hepatocytes; HBV is hepatotropic. However, one may engineer a heterologous promoter/enhancer element for HBV expression and replication in a non-hepatocyte system. For example, one may use non-hepatocyte systems, such as fibroblast, lymphocyte, Hela, and transgenic animals/plants.

The HBV-defective interfering viruses are not limited to pDEL85 or pDEL109 (FIG. 1) in this patent application. Other HBV-defective interfering viruses, such as, but not limited to, those with a different length of deletion or degree of defective interfering effect, an out-of-frame deletion, within or outside core antigen, can also be prepared by those having ordinary skill in this art.

The SV40 expression vector of wild type HBV core antigen has been constructed (FIG. 2). Different expression vectors, such as those with inducible promoters or more potent promoters, can also be used, as would be well known by those having ordinary skill in this art.

The rescued defective interfering particles can be enveloped and secreted into the tissue culture medium (FIG. 2). The medium can be harvested by methods, such as centrifugation, filtration, PEG precipitation, or passing through columns of anti-surface antibodies; whichever is the most cost-effective.

For the purification of DI viruses, various techniques may be used. For example, DI viruses from conditioned medium (e.g., 24–48 hour incubation) can be harvested in a number of ways. Existing protocols for the purification of the 22 nm HBsAg particles can be modified or adopted to purify the DI virus particles. For example, the following steps in different combination and orders can be used. The efficiency of each step involved in the purification scheme is monitored by examining the deleted core gene DNA fragment via PCR amplification (Example 1). One important caveat is to purify the DI virus preparation without losing the biological activity and infectivity of DI viruses. Therefore, existing protocols for the biochemical purification of HBV surface antigen molecules (a non-life form) is not necessarily the best or even applicable for the biological purification of DI viruses (a life form, especially if it is to be used for treatment of fulminant hepatitis patients).

Centrifugation methodology is described in Example 4. For adsorption onto colloidal silica such as aerosil (which is optional), it is unclear if the DI virus can adsorp to aerosil. If they do, after adsorption and washing, DI virus can be eluted from the silica by warm borate buffer. This step is optional since centrifugation steps described above might he sufficient to reduce the process volume, enrich DI virus particles and remove debris and serum proteins.

Size exclusion, ion exchange, or hydrophobicity (e.g., butyl agarose or sepharose) chromatography methods can be used if they are more cost-effective, simpler or easier than centrifugation. PEG-precipitation, i.e., the precipitation of viruses using PEG6000 at 4° C. for a period of hours may also be used.

Immunoaffinity chromatography, e.g., using a two column system may also be used. The first column consists of anti-HBV envelope antibody attached to Sepharose and eluted with 3M NASCN.

The second column contains sheep or rabbit anti-bovine serum antibodies designed to remove any residual contamination of bovine serum proteins with the virus preparation. Pepsin treatment at pH2 can be used to remove and degrade contaminants from bovine serum, although dialysis of the DI virus preparation against PBS at 4° C. overnight will be sufficient, Formulation of the DI virus into a vaccine or therapeutic agent can be accomplished by kepping the DI virus prepagation in sterile PBS. Sterilization can be done by filtration throuhgh a 0.22 μm membrane. Long term storage could include the use of 10% glycerol or DMSO in PES in liquid nitrogen. Short term storage could be in 4° C. or −20° C. It is also possible that glycerol and DMSO are not necessary. Frozen vials of DI viruses should be administerd as soon as they are thawed at room temperature or 37° C. For large scale purpose, tissue culture systems, such as microcarriers, can be tested. Long term storage of defective interfering viruses can be attempted using 10% glycerol or DMSO in the presence of serum and medium (e.g., DMEM) at −70° C. or in liquid nitrogen.

In general, defective interfering-viruses cannot be separated from the helper viruses. The prior art of isolation of defective interfering variants of rhabdoviruses from the infectious helper viruses utilized rate zonal sucrose centrifugation (Huang et al., '66). The present invention discloses a novel approach to make defective interfering virus preparations which does not require the use of a laborious separation step via centrifugation from helper viruses. Most importantly, separation of defective interfering from infectious helper viruses always has a risk of contamination of defective interfering preparation by trace amounts of infectious helper viruses. This approach is much safer than prior art since only the replication defective defective interfering will be rescued and secreted, and there is no chance of contamination of defective interfering preparation by infectious helper viruses.

The following examples are given for the purpose of illustrating various embodiments of the invention and are not meant to limit the present invention in any fashion.

EXAMPLE 1
Preparation of DNA from liver tissues and amplification by PCR and detection of the core deleted variant by Southern blot For construction of plasmids, pSV2ANeo-HBV dimer containing two head-to-tail copies of HBV genome was used as a wild type HBV expression vector. The fragments from nucleotide 1636 to nucleotide 2688 of pdel85 and pdel109 were amplified from tumor samples, T85 and T109, by PCR with two oligonucleotides. One 30-mer (5'-AAGGGCAAATATTTGGTAAGGTTAGGATAG-3') contains HBV minus-strand DNA aequence from nucleotide 2659 to nucleotide 2688 with a intrinsic SspI cleavage site (underlined). The other primer is a 27-mer (5'-AGAAATATTGCCCAAGGTCTTACATAA-3') containing HBV plus-strand DNA sequence from nucleotide 1636 to nucleotide 1659 with a created SspI cleavage site (underlined). One microgram of tumor DNA and 100 ng of each primer were used in a 10-μl PCR reaction consisting of a denaturing cycle at 94° C. (20 sec) followed by a 40-cycle amplification at 94° C. (1 sec), 47° C.(1 sec), and 72° C. (40 sec). The amplified target sequence (0.9 kb) was subcloned into the pGEM-T vector (purchased from Promega) and secreened for clones containing HBV deleted core sequence by DNA sequencing. The characterized fragment which contains HBV deleted core sequence was purified by digestion with SspI and subsequently swapped for the counterpart of wild type HBV genome carried on a puc12-HBV monomer (HW-1). The dimerization of the core deleted HBV genome was achieved by ligating the EcoRl site spanning fragment (3 kb) of the puc12-HBV deletion monomer back to the downstream EcoRI site of the same plasmid. The resulting dimer constructs, pdel85 and pdel109, were then characterized by restriction enzyme digestion and DNA sequencing was performed for the entire core regions (data not shown).

To construct pSVC, the PCR amplified core fragment from nucleotide 1877 to nucleotide 2463 was digested with restriction enzymes HindIII and SacI and subdloned into the HindIII and SacI sites of the parental plasmid pGCE under the control of the SV40 enhancer and early promoter (Pei., 1991). Two oligonucleotides were used for PCR reaction. One 30-mer (5'-AGAAAGCTTAGCTGTGCCTTGGGTGGCTTT-3') contains HBV plus-strand DNA sequence from nucleotide 1877 to nucleotide 1897 with a HindIII cleavage site (underlined). The other primer is also a 30-mer (5'-AGAGAGCTCATACTAACATTGAGATTCCCG-3') containing A SacI cleavage site (underlined). One nanogram of pSV2ANeo-HBV monomer and 100 ng of each primer were used in a 10 μl PCR reaction consisting of a denaturing cycle at 94° C.(20 sec) followed by 40-cycle amplification at 94° C. (1 second), 53° C. (1 second), and 72° C. (40 second).

To construct p1903, site-direct mutagenesis was performed using plasmid RG6 containing a full-length HBV monomer DNA (Roychoudhury, 1990) and a oligonucleotide (5'- -3') which eliminated the ATG translational start codon of the core region. The procedure for site-direct mutagenesis was adapted from that of Kunkel (Kunkel, 1985) and the dimerization of the HBV genome was described elsewhere (Roychoudhury, 1990).

EXAMPLE 2
Cell culture and transfection

The human hepatoma cell line Huh7 was maintained in Dulbecco's modified Eagle's medium (DMEM) with 10% fetal bovine serum at 37° C. in the presence of 5.5% $CO_2$. The calcium phosphate transfection procedure was detailed elsewhere (Shih, 1989). Briefly, $10^6$ cells per 10-cm dish were transfected with certain amount of assayed DNA plus human genomic DNA to a total amount of 35 μg. Donor DNA was removed at about 6 hours post-transfection, and cells were fed with fresh DMEM containing 10% fetal bovine serum.

EXAMPLE 3
Preparation of intracellular core particles

The procedure used to prepare intracellular core particles was described in detail (Roychoudhury, 1991). At 5 days post-transfection, cells from one 10-cm dish ($6 \times 10^6$ cells) were lysed at 37° C. (15 minutes) in 1 ml of buffer containing 10 mM Tris hydrochloride (pH 7.5), 1 mM EDTA, 50 mM NaCl, 0.25% Nonidet P-40, and 8% sucrose.

The lysate was then spun in a microcentrifuge for 2 minutes, and the supernatant was transfered to another tube. The supernatant was brought to 8 mM $CaCl_2$ and 6 mM $MgCl_2$, followed by digestion with 30 U of micrococcal nuclease and 1 U of DNase I at 37° C. (15 minutes). The crude core particles were then precipitated by adding 330 μl of 26% polyethylene glycol (molecular weight 8000) in 1.5M NaCl and 60 mM EDTA. After incubation for 1 hour at 4° C., the crude core particle preparations were pelleted by spinning in microcentrifuge for 4 minutes.

EXAMPLE 4
Collection of extracellular core particles

Extracellular core particles were collected 5 days post-transfection from a 10-cm dish of 48-hour conditioned media (10 ml). The medium was precleared by spinning at 3,200 rpm for 15 min. in a IECCentra-8 centrifuge. Particles from the clarified medium were pelleted through a 16-ml cushion of 20% sucrose by spinning at 25,000 rpm for 16 hours at 4° C. in a Beckman SW28 rotor.

EXAMPLE 5
Preparation of core associated DNA

The core pellet was resuspended in 100 μl of buffer containing 10 mM Tris (pH 7.5), 8 mM $CaCl_2$, and 6 mM $MgCl_2$. The suspension was then treated with 30 U of micrococcal nuclease and 1 U of DNase I for 15 minutes at 37° C. Core particles were lysed by the addition of 300 μl of lysis buffer containing 25 mM Tris (pH 7.5), 10 mM EDTA, and 1% SDS in the presence of protinase K at a final concentration of 400 μg/ml. After incubation at 50° C. for 1 hour, DNA was phenol and chloroform extracted and ethanol precipitated.

EXAMPLE 6
Preparation of core associated RNA and total RNA

Briefly, the core pellet was first dissolved in 100 μl of denaturation solution (4M guanidine thiocyanate, 25 mM sodium citrate, 0.5% Sarkosyl, 0.1M 2-mercaptoethanol). Following dissolution, 10 μl of 2M sodium acetate (pH 4.0) and 100 μl of water-saturated phenol were added with mixing of the solution by inversion. Finally, 20 μl of a chloroform-isoamyl alcohol mixture (49:1) was added and vortexed for 30 sec. The whole mixture was kept on ice for 15 minutes and then centrifuged for 15 minutes at 4° C. The resulting aqueous phase was transfered to another tube, and RNA was precipitated by the addition of an equal volume of isopropanol. For isolation of total RNA, cells from a 6-cm dish were lysed in 350 μl of denaturation solution 2 days post-transfection, and the volume of the rest of the solutions were adjusted accordingly.

EXAMPLE 7
Primer extension analysis

A 5'-end-labeled 22-nucleotide synthetic oligonucleotide (nucleotide 1980 to nucleotide 2001) was used as a primer. Approximately $10^5$ cpm (0.1 pmol) was lyophilized with half of core-associated RNA isolated from one 10-cm dish. The dried pellet was dissolved in 30 μl of hybridization buffer containing 40 mM PIPES [piperazine-N,N'-bis(2-ethanesulfonic acid)] (pH 6.4), 400 mM NaCl, 1 mM EDTA, 80% formamide. The hybridization mixture were heated up to 85° for 10 minutes and quickly transferred to a water bath at 30° for 2 hours. After annealing, 170 μl of water and 400 μl of ethanol were added for precipitation. The washed and dried pellet was then dissolved in 20 μl of reverse transcription buffer (50 mM Tris hydrochloride [pH 8.5], 8 mM $MgCl_2$, 30 mM KCl, 1 mM dithiothreithol, 1 mM of four deoxynucleotide triphosphates, 50 μg of actionmycin D per ml, 10 U of human placental RNase inhibitor) and incubated with 25 U of reverse transcriptase from avian myeloblastosis viruses (Boehringer Mannheim GmbH) at 45° for 90 minutes. The reaction was terminated by the addition of 1 μg of 0.5M EDTA, and the RNA was digested with 1 μg of pancreatic RNase A at 37° C. for 30 minutes. A 100 μl volume of 2.5 mM ammonium acetate was then added, followed by phenallchloroform extraction and ethanol precipitation. The washed and dried pellet was dissolved in 3 μl TE (10 mM Tris hydrochloride [pH 7.5], 1 mM EDTA), and 4 μl of loading buffer (80% formamide, 1 mM EDTA, 0.1% bromophenol blue, 0.1% xylene cyanol) was added. A 3-μl portion of each sample was analysed on a 6% polyacrylamide sequencing gel.

EXAMPLE 8
In vitro translation, CAT assay and Southern (DNA) and Northern (RNA) analyses Southern and Northern blot analyses followed standard procedure (Maniatis, 1989). Filters were probed with a vector-free $^{32}$P-labeled full-length HBV DNA fragment (3.1 kb).

EXAMPLE 9
Western (protein) blot analysis and antibodies

Immunoblot procedure was adapted from Harlow and Lane (1988). Cells from one 6-cm dish were lysed at 3 days posttransfection with 150 μl 2× loading buffer (0.5M Tris hydrochloride [pH 6.8], 2% SDS, 5% β-mercaptoethanol, 20% glycerol, and 0.0025% bromophenol blue), and one 25-μl aliquot was subjected to SDS-PAGE electrophoresis before transfering to nitrocellulose (Schleicher and Schuell). The blotted filter was blocked with 2% nonfat milk in PBS for 30 minutes at room temperature. The blocked filter was incubated with primary antibody overnight at 4° C., and then washed 3 times with 5 minutes interval with PBS containing 0.05% Tween 80 (TW80/PBS). Rabbit anticore antiserum was developed by Dr. Lanford (Lanford, 1987) and mouse antiPS-1 antiserum was developed by Dr. Gerlish. After TW80/PBS wash, the blot was rinsed with cold PBS and then incubated with 0.25% glutaradehyde in PBS for 15 minutes at 4° C. After briefly rinsed with cold PBS, the blot was reblocked with the buffer containing 0.2% BSA and 0.1M glycine in PBS (pH 8.5) for 20 minutes at room temperature. Either goat anti-rabbit or goat anti-mouse antiboy conjugated with horseradish peroxidase (BIO-RAD) was applied to the blot and incubated for 2 hours at room temperature. The filter was washed 3 times with TW80/PBS and then developed using ECL kit as recommended by the manufacturer (Amersham).

EXAMPLE 10
Sedimentation and fractionation of virus particles: Surface and e Ag assays Abbott HBe (rDNA) EIA and Auszyme Monoclonal kits were used for the immunoassay of e and surface antigens according to the manufacturer's procedure (Abbott Laboratory).

EXAMPLE 11
Construction of HBV-CID plasmids

In studies (Hosono et al., '95), HBV-CID mutants were identified in Taiwanese HCC patients T61 and T109. The internal deletion of core antigen of T61 and T109 ranges from around codons 80 to 120. The present invention identified a third CID mutant from patient T85, which contains an even larger deletion (codons 89–136) by extending into the adjacent hotspot mutational domain V.

Figure 5A:
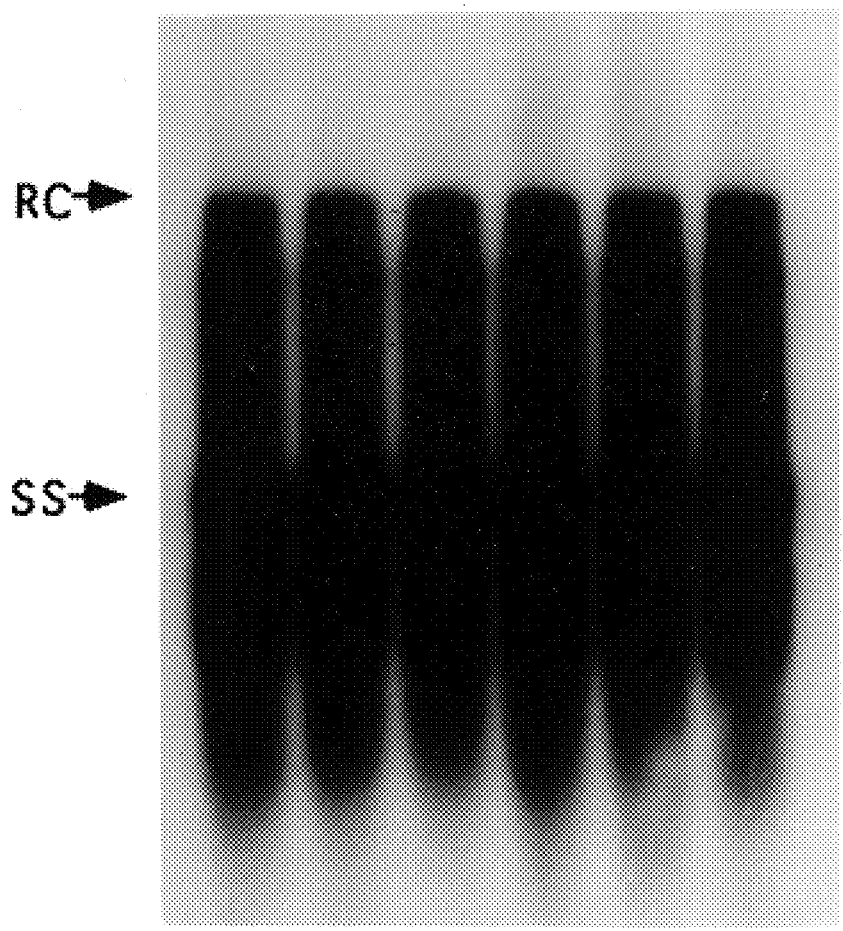
Figure 5B:
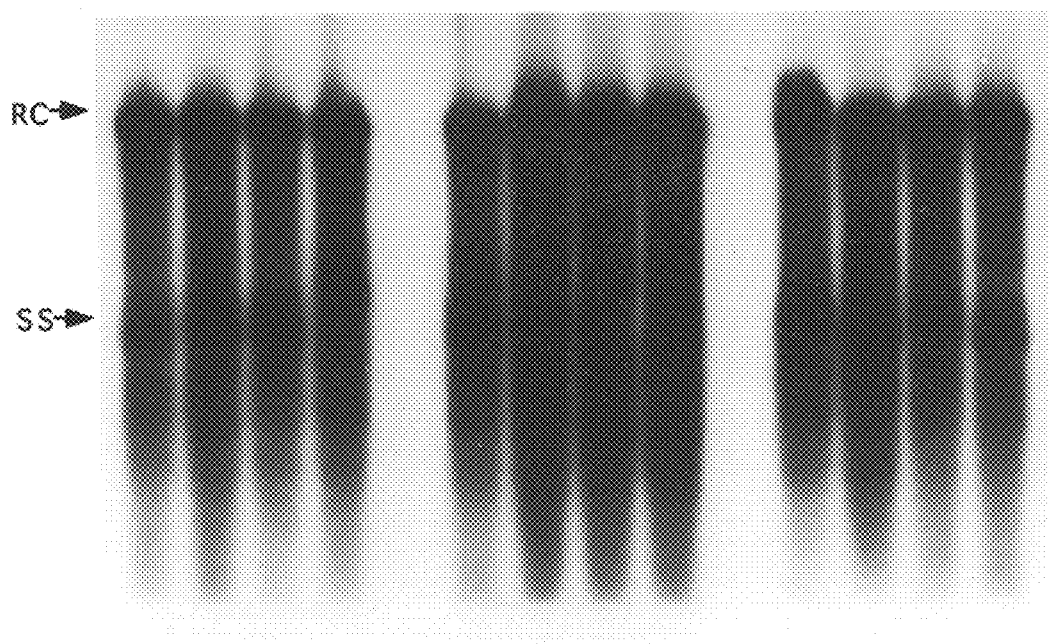

The deletion-containing HBcAg fragments of T85 and T109 were PCR-amplified and substituted with the normal counterpart of a wild type HBV plasmid (Shih et al., '89). To mimic the circular configuration of HBV genome, the monomeric recombinant chimera between CID and wild type were dimerized in tandem. The tandem homodimer plamids are abbreviated as pDEL85 and pDEL109, respectively. DEL85 deleted HBcAg amino acids 88 to 135 while DEL109 lost amino acids 82 to 122 (FIG. 1A). The construction of these plasmids has been confirmed by DNA sequencing across the recombinant junctions.

EXAMPLE 12

Replication and Packaging Defects of HBV-CID Mutants

To see if the CID mutants are viable by itself, either DEL85 or DEL109 alone were transfected into a human hepatoma cell line Huh7. As shown in FIG. 1B, both mutants are replication defective by Southern blot analysis. The deficiency in DNA synthesis is due to their defect in RNA encapsidation as indicated by primer extension analysis using encapsidated pregenomic RNA (FIG. 1C). Productive pregenomic RNA encapsidation requires at least three different viral components: nucleocapsid protein, polymerase and the 3.5 kb pre-genomic RNA.

To identify the defect of CID mutants in encapsidation, the steady state level of the pregenomic RNA was first examined by Northern blot analysis (FIG. 1D). No significant difference between wild type and CID mutants was detected. The deletion endpoints of a-DEL109 is 15 amino acids upstream from the translational initiation codon (AUG) of polymerase (Hosono et al., '95) while the deletion endpoint of DEL85 is exactly next to the AUG initiation codon of polymerase (nucleotide sequence data not shown; see FIG. 7B for amino acid sequence). Therefore, the open reading frames of polymerase in both CID mutants are not directly affected by the core internal deletions.

To measure the low level expression of polymerase, a fusion construct was engineered between polymerase and the reporter gene of chloramphenicol acetyltransferase (CAT). Again, no appreciable difference of CAT activities between CID mutants and wild type was detected (FIG. 1E). Finally, the production of nucleocapsid proteins from either wild type or CID mutants was examined. The defect in RNA encapsidation of CID mutants is correlated with the absence of a 22 kD or lower molecular weight HBcAg protein by immunoblot analysis (FIG. 1F).

EXAMPLE 13

CID mutants are Rescuable by Wild Type Core Protein

The fact that these replication-defective CID mutants can be detected in patients by PCR suggested that they might be able to survive in the presence of other HBVs. CID mutants were cotransfected with a wild type HBcAg expression vector. Both CID mutants can be rescued to at least 80% level of wild type replication activity (FIG. 2A). These rescued CID mutants can also be secreted into the medium (FIG. 2B). The sedimentation profile of these rescued and secreted CID viral particles on gradient centrifugation by Southern blot analysis was almost indistinguishable from wild type in the Dane particle fractions (FIGS. 4C and D). The presence of the core gene deletion in the rescued and secreted Dane particle fractions was confirmed by PCR amplification (data not shown).

EXAMPLE 14

Interference and Enrichment

As shown in FIG. 3A, when increasing amounts of CID mutants were cotransfected with wild type HBV, the replication activity of HBV remains more or less constant by Southern blot analysis using the full-length HBV DNA probe. However, the relaxed circle form of HBV replicative intermediate purified from cotransfected culture reproducibly migrates slightly faster than that from cultures transfected with wild type DNA alone.

The same filter of FIG. 3A was washed and reprobed with a wild type-specific DNA fragment from within the internally deleted region of HBcAg gene (FIG. 3B). This probe should not hybridize with the CID mutant DNAs. In contrast to the results in FIG. 3A, in the presence of equal amount of CID mutant DNAs, wild type specific DNA replication was reduced by approximately 7 fold in the case of DEL85 and approximately 3 fold by DEL109. As a control for nonspecific effects, such as squelching of limiting amount of cellular transcription factors, a packaging and replication defective HBV mutant TGAGC was included for comparison (Yuan et al., '95). No apparent reduction of wild type replication was observed by cotransfection with mutant TGAGC (FIG. 3B). To directly demonstrate that the signals of HBV replication in cotransfection experiment in FIG. 3A was largely due to the replication of CID mutants, the same filter was probed with mixtured probes specific for DEL85 and DEL109. Consistent results were obtained (FIG. 3C). Taken together, FIGS. 3A–C indicated that while the CID mutant is increased in proportion, wild type replication is greatly reduced.

To show that the defective interfering-like behavior of HBV-CID mutants was not idiosyncratic to Huh7 cell line, the same experiment were repeated using another replication-permissive human hepatoblastoma cell line HepG2. Similar results were obtained in HepG2 system although the defective interfering effect appears to be even stronger in HepG2 than Huh7, as indicated by a 10 to 16 fold reduction in wild type replication (FIG. 3D). This defective interfering phenomenon, including interference of wild type and enrichment of CID mutants was also evident when extracellular HBV particles was examined using the full-length HBV probe (FIG. 3E) or wild type-specific probe (FIG. 3F). In general, the defective interfering effect of DEL85 was more potent than that of DEL109 (FIG. 3B and 3D). FIG. 3G shows a cartoon illustration of the wild type-specific and DEL- specific probes used.

EXAMPLE 15

PCR analysis before and after transfection

To confirm the results obtained by Southern blot analysis, a PCR assay was used to measure directly the relative population of wild type helper virus and CID variants in the cotransfection experiment. When a mixture of the donor DNAs (pWT and pDEL85) in the 2:1 dose ratio was used in the PCR assay, the wild type-specific DNA fragments exhibited similar intensity to that of the DEL85 deleted fragment after amplification (FIG. 4, top). This is probably because the shorter (deleted) DNA fragments tend to be amplified favorably during PCR. However, the relative intensity between amplified wild type and mutant DEL85 DNA fragments shifted from 1:1 (before cotransfection) to 1:5 (after cotransfection), suggesting the preferential de novo replication of CID variants over wild type HBV in vivo (FIG. 4, bottom).

EXAMPLE 15

Specific vs. Nonspecific Interference

Based on the enrichment phenomenon of CID mutants, one would conclude that the interference on wild type is probably not caused by a nonspecific effect, such as different degree of resistance to cytotoxicity or defective interfering-induced interferon-like soluble factors to which wild type is perhaps more sensitive. Consistent with this, FIG. 5A showed that the conditioned media of CID mutant-transfected culture did not confer any apparent interference effect when applied to the wild type HBV transfected culture. Furthermore, when duck hepatitis B virus DNA was cotransfected with human CID mutants, no apparent decrease of duck hepatitis virus DNA replication was observed (FIG. 5B). The DNA probe of duck hepatitis virus does not cross react with human HBV even at highly relaxed stringency (data not shown). Therefore, the interference phenomenon of HBV-CID appears to be homotypic and species-specific. In summary, as characterized above, the properties of CID mutants seem to fit well with the conventional definition of defective interfering particles: deleted genome, replication defective, rescuability by helper viruses, and enrichment of themselves at the expense of helper viruses (Huang & Baltimore, '70).

EXAMPLE 16
Highly Unstable CID-HBcAg and e Antigen

Figure 1F:
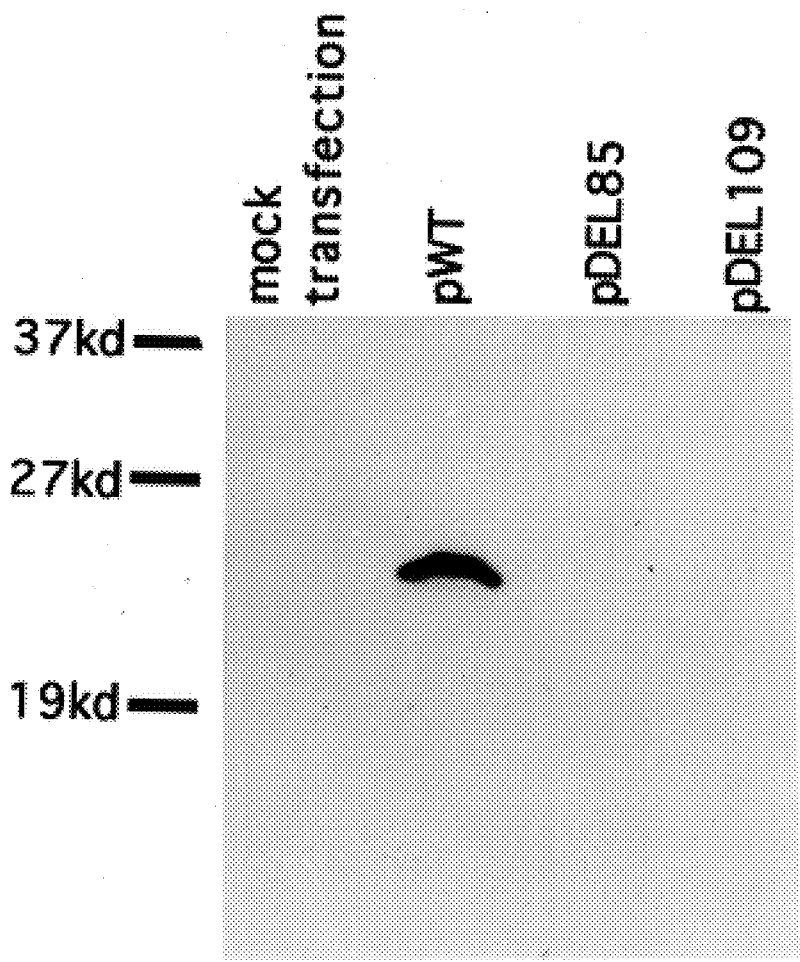
Figure 2A:
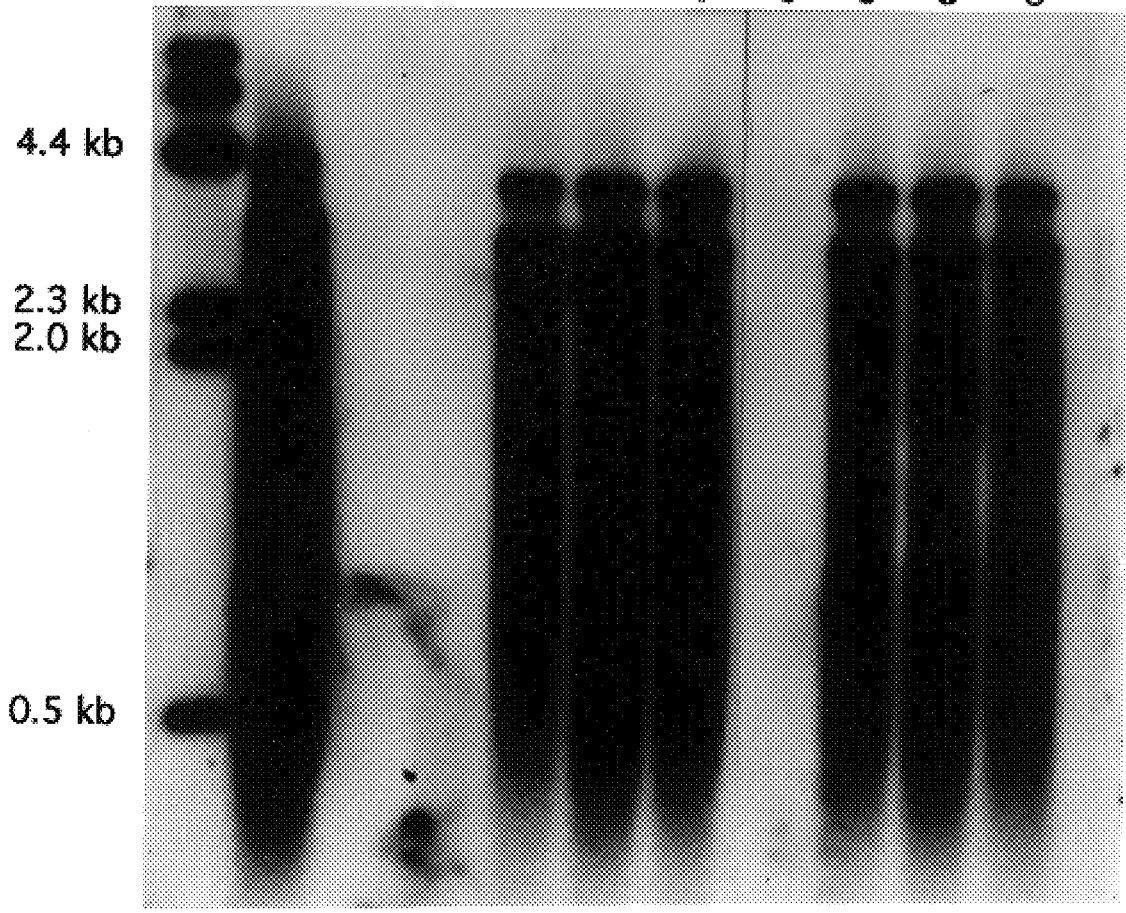
Figure 2B:
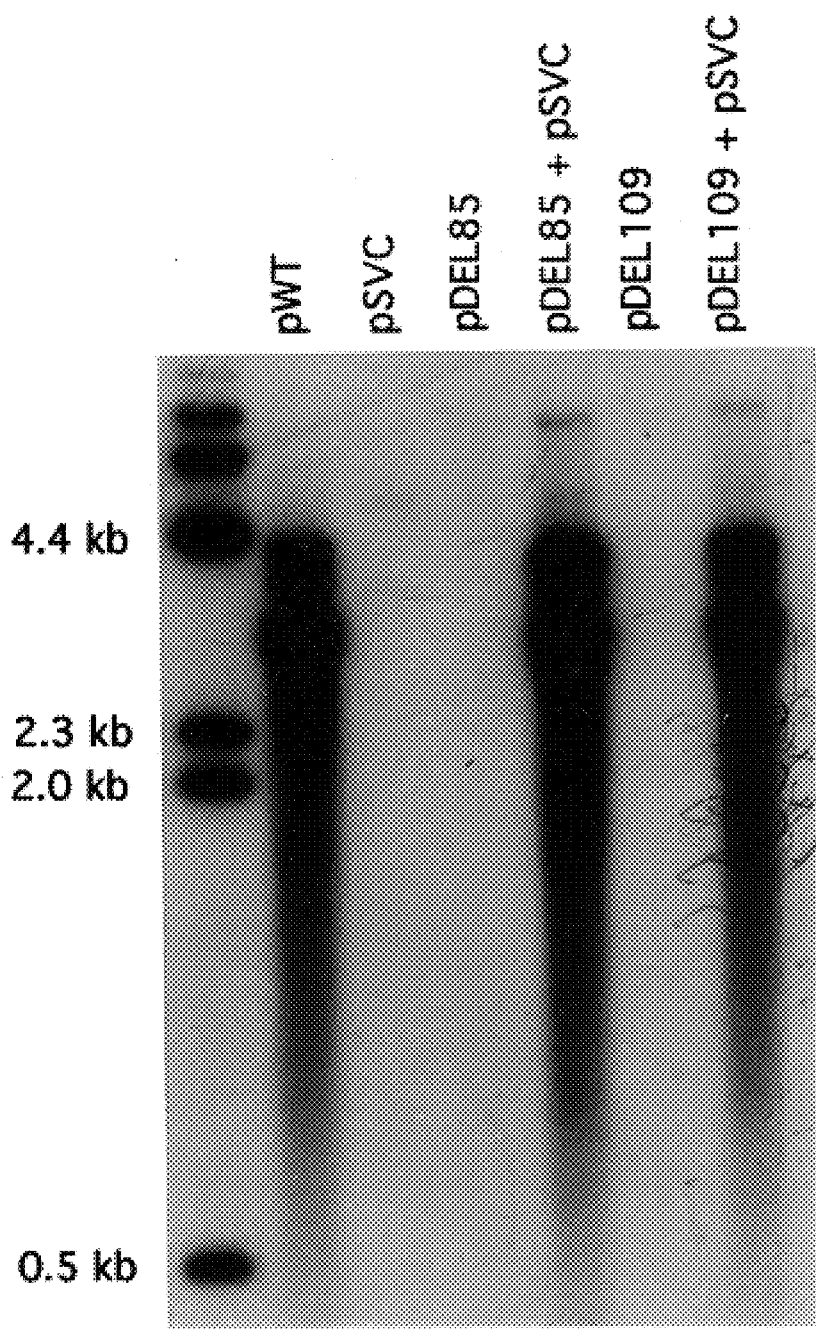
Figure 2C:
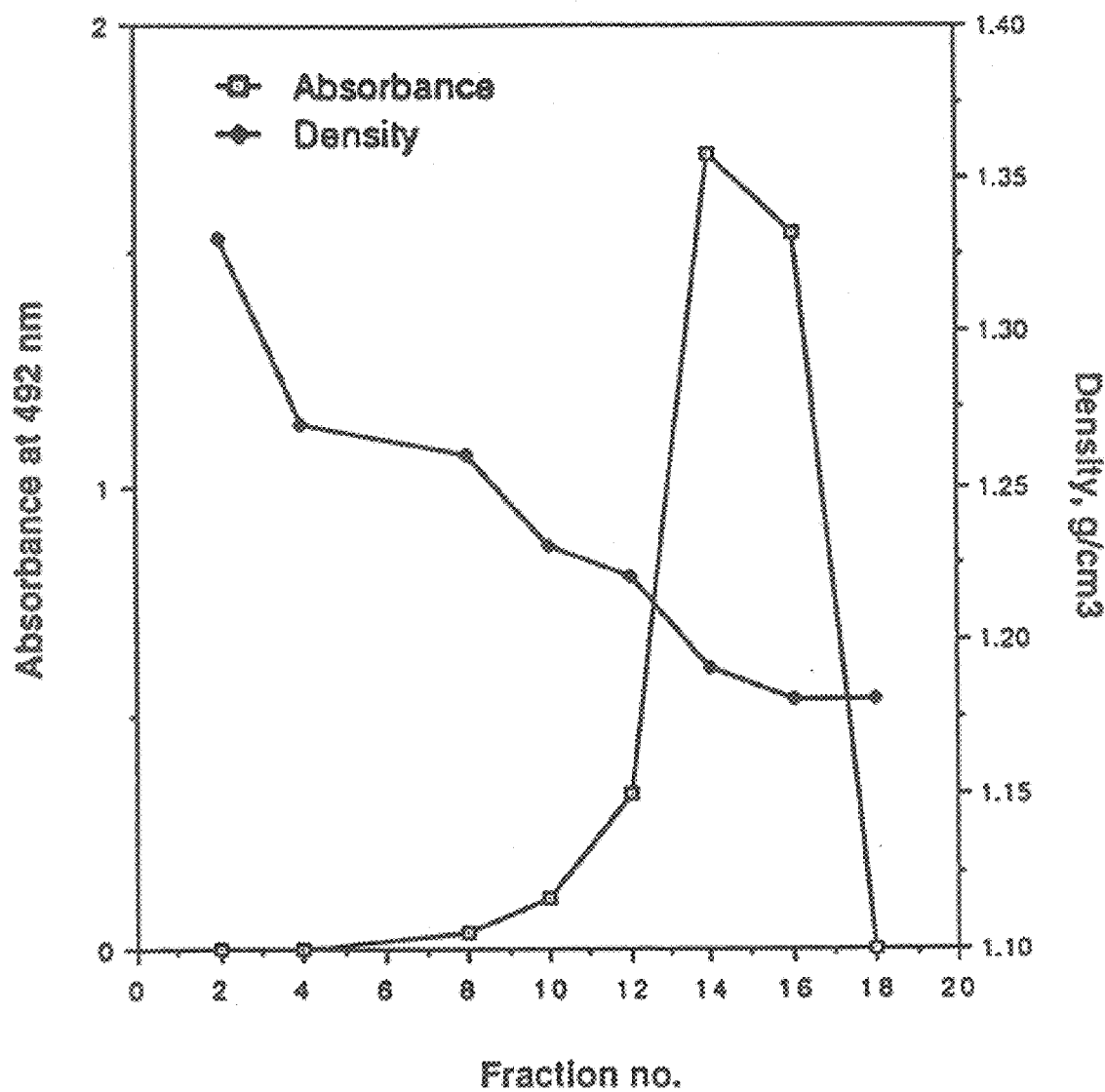
Figure 2C:
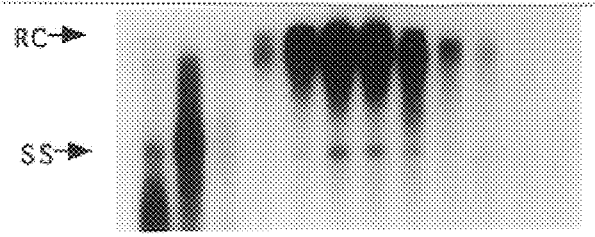
Figure 2D:
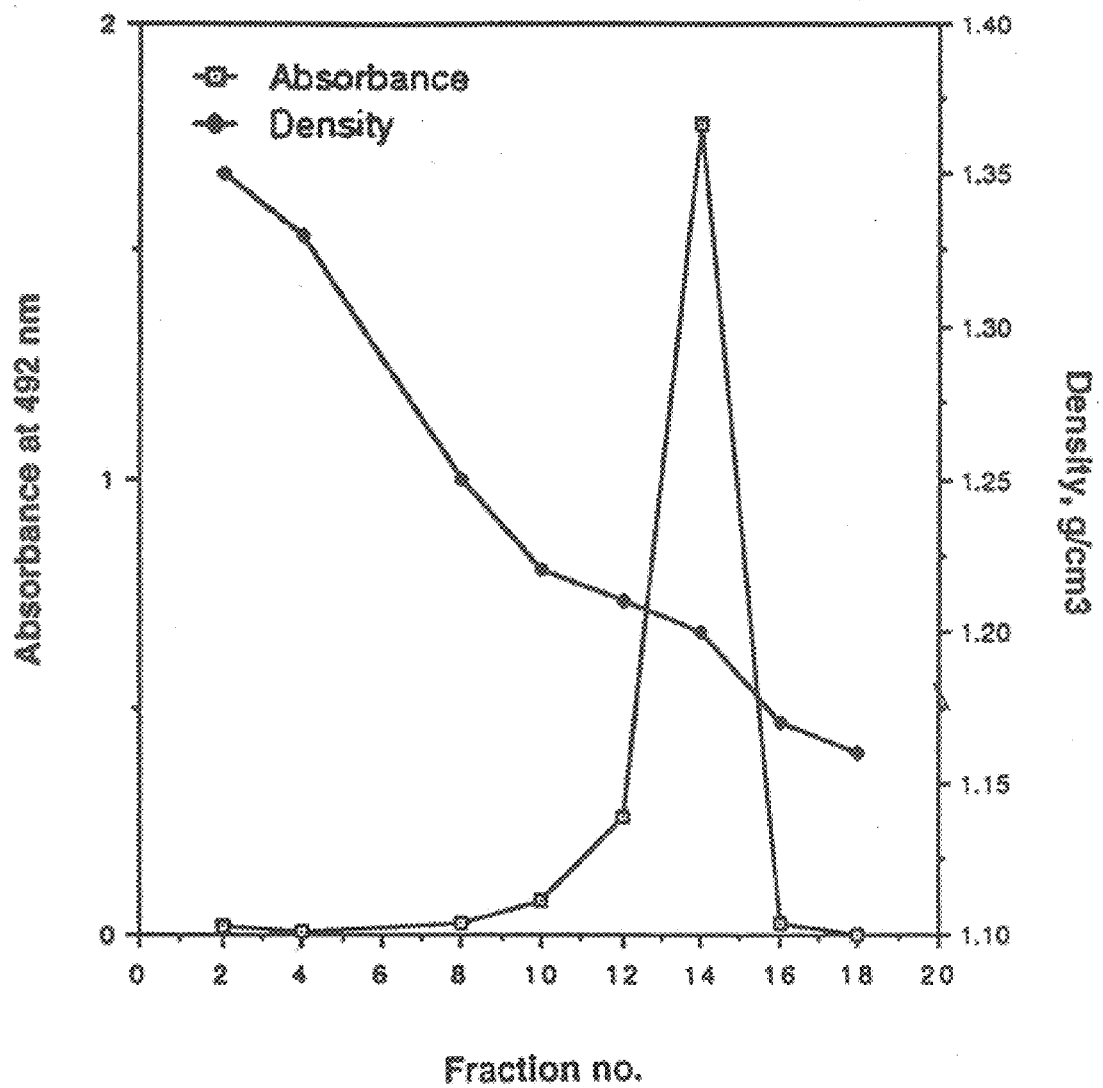
Figure 2D:
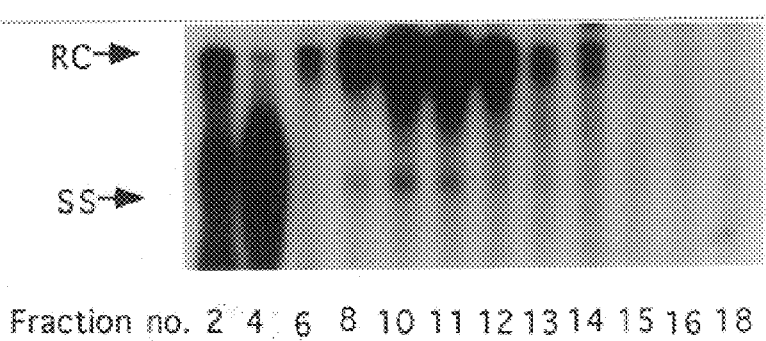

One mechanism for the interference phenomenon of HBV CID mutants is the dominant negative effect on the wild type HBV mediated through the deleted core protein. The existence of the internally deleted core antigen was determined by immunoblot analysis using a polyclonal anti-HBcAg antibody. Despite the use of different anti-HBcAg antibodies, no core protein was detected from the CID mutant (FIG. 1F). This negative result could be due to a number of possibilities, such as loss of a dominant antibody recognition site and/or instability of the produced mutant core protein.

Figure 6A:
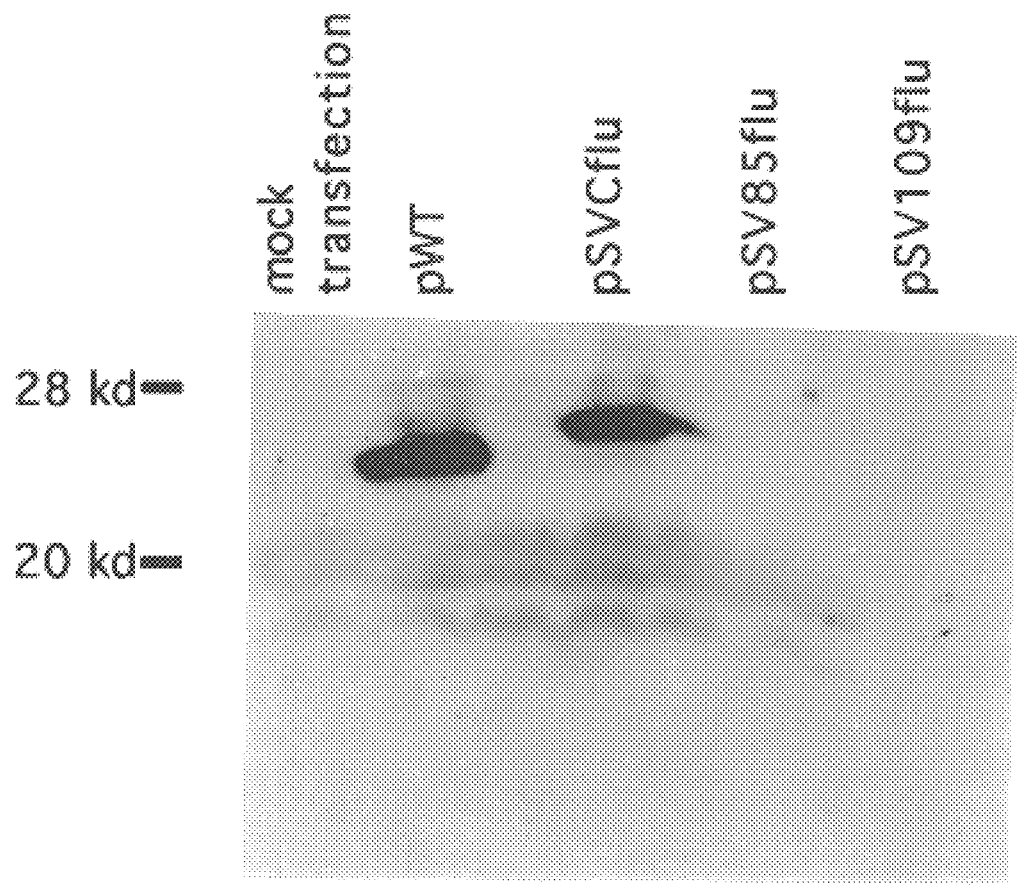
Figure 6B:
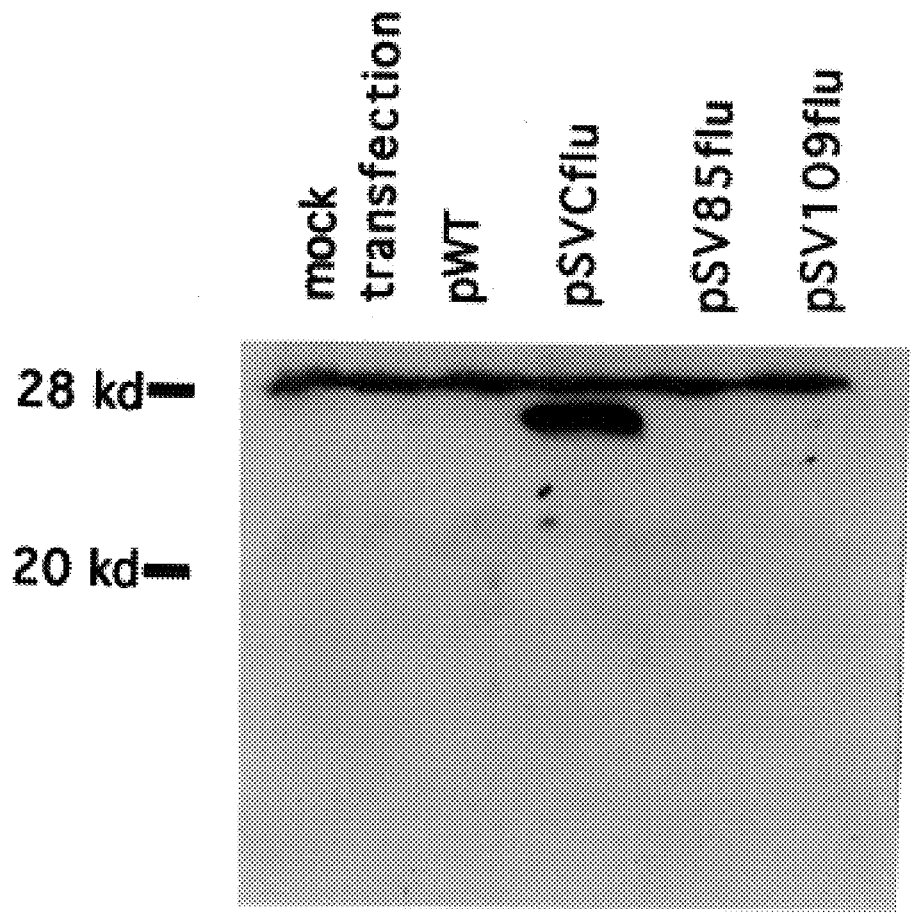
Figure 6C:
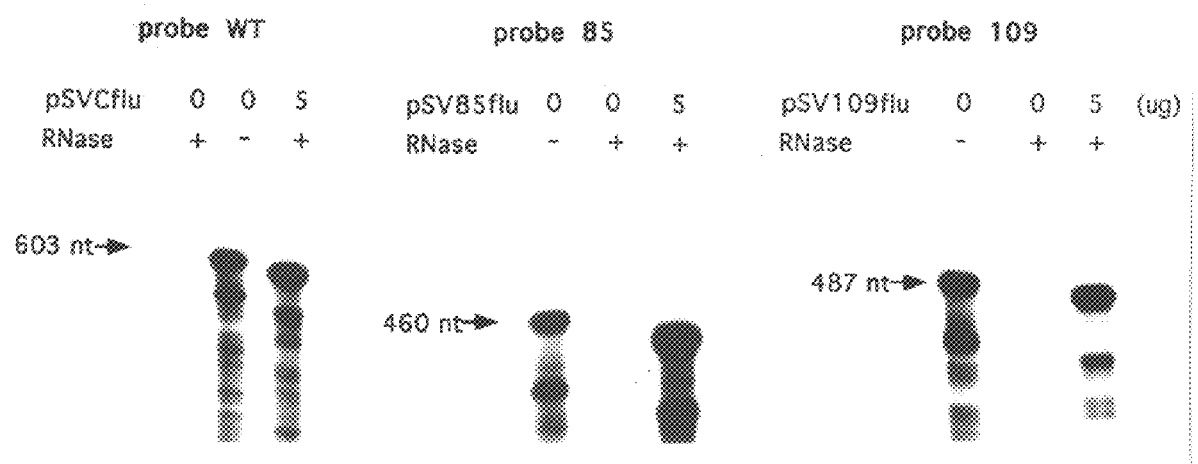

To differentiate among these possibilities both the deleted and wild type core proteins, were tagged with a flu epitope. As shown in FIG. 6, wild type core-flu fusion protein can be detected by either anti-core (FIG. 6A) or anti-flu antibodies (FIG. 6B). In contrast, CID core-flu fusion proteins cannot be detected by either antibodies, despite the stable expression of CID mutant core-flu mRNAs from plasmids pSV85flu and pSV109flu (FIG. 6C). Therefore, the loss of a dominant anti-core antibody recognition site alone is a less likely explanation for the absence of CID-specific core protein.

Figure 6D:
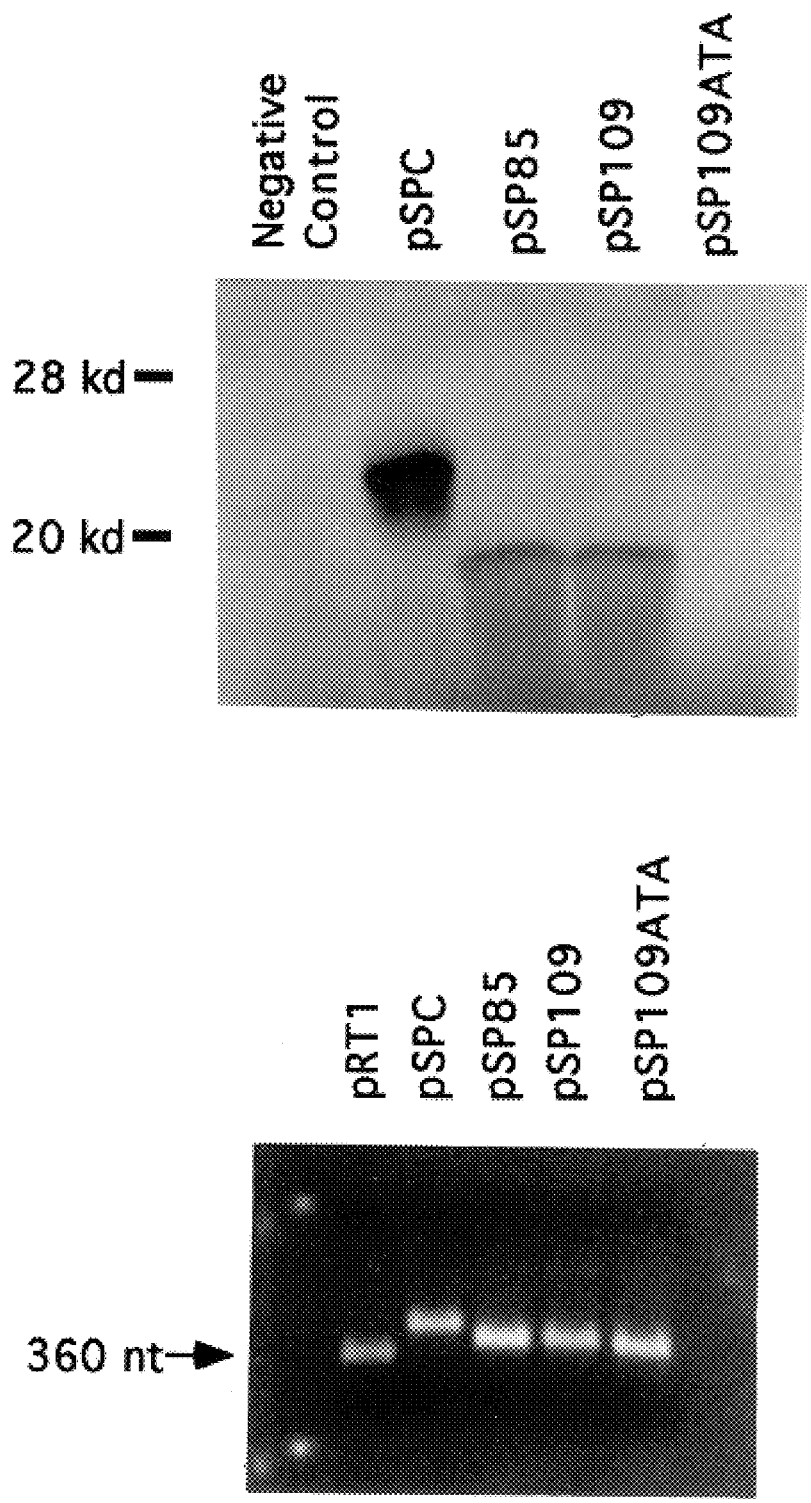
Figure 6E:
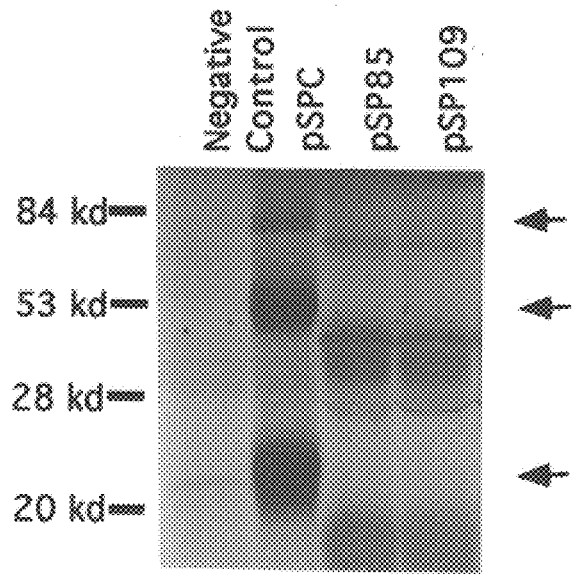

However, using an in vitro transcription and translation assay, CID mutant core protein with a reduced molecular weight can be expressed in vitro, albeit with a lower intensity relative to the wild type core protein. Furthermore, when the ATG initiation codon of the CID core protein is ablated by changing into ATA, no translated protein was observed (FIG. 6D). When the wild type and deleted core proteins were analyzed under non-denaturing condition, CID core proteins appeared to homopolymerize more readily than wild type core protein (FIG. 6E). Taken together, these results are consistent with the interpretation that the CID core protein is highly unstable in vivo and in vitro.

The core antigen is structurally related to HBV e antigen. Because core and e antigens share the same open reading frame, the CID deletion not only creates an unstable core protein, but also an unstable e antigen. No production of e antigen from CID variants were detected using Abbott EIA kit. Therefore, CID mutant DEL85 and DEL109 exhibited an e antigen negative phenotype (data not shown). Absence of e antigen has been proposed to be associated with fulminant hepatitis (Shafritz et al., '91). The biological function of e antigen is not fully understood; nontheless, it may be involved in HBV pathogenesis (Milich et al '90; Carman et al., '89).

EXAMPLE 17
No Dominant Negative Effect of CID-Core Antigen

Dominant negative mutants of hepadnaviruses have been artificially created by fusing the core and surface genes (Scaglioni et al., '94), or by deleting part of the DHBV core antigen (Horwich et al., '90). One essential feature of the defective interfering viruses is their enrichment behavior. Although the dominant negative mutants can interfere with the replication of wild type, they are not able to enrich themselves at the expense of the wild type. Therefore, it is unlikely that the defective interfering phenomenon is mediated through a dominant negative effect.

Figure 6F:
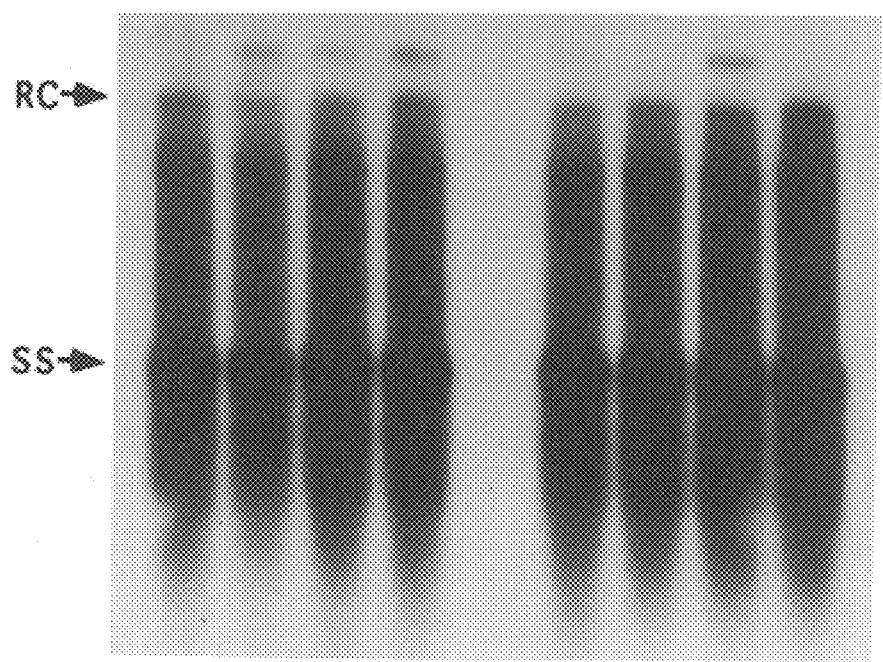

To demonstrate whether the defective interfering phenomenon could be (solely) caused by the deleted core protein via a dominant negative effect, wild type HBV was cotransfected with an expression vector of CID mutant core protein (pSV109). As a control, a derivative of pSV109 with an ablated initiation codon changing from ATG to ATA were also cotransfected in parallel wild type and pSV109ATA. No apparent reduction in wild type HBV replication was observed when pSV109 was used (FIG. 6F). This result is consistent with the aforementioned high instability of CID mutant core protein in vivo. In summary, the interference phenomenon of CID mutant does not appear to be caused by any dominant negative effect through the deleted core protein.

Figure 7A:
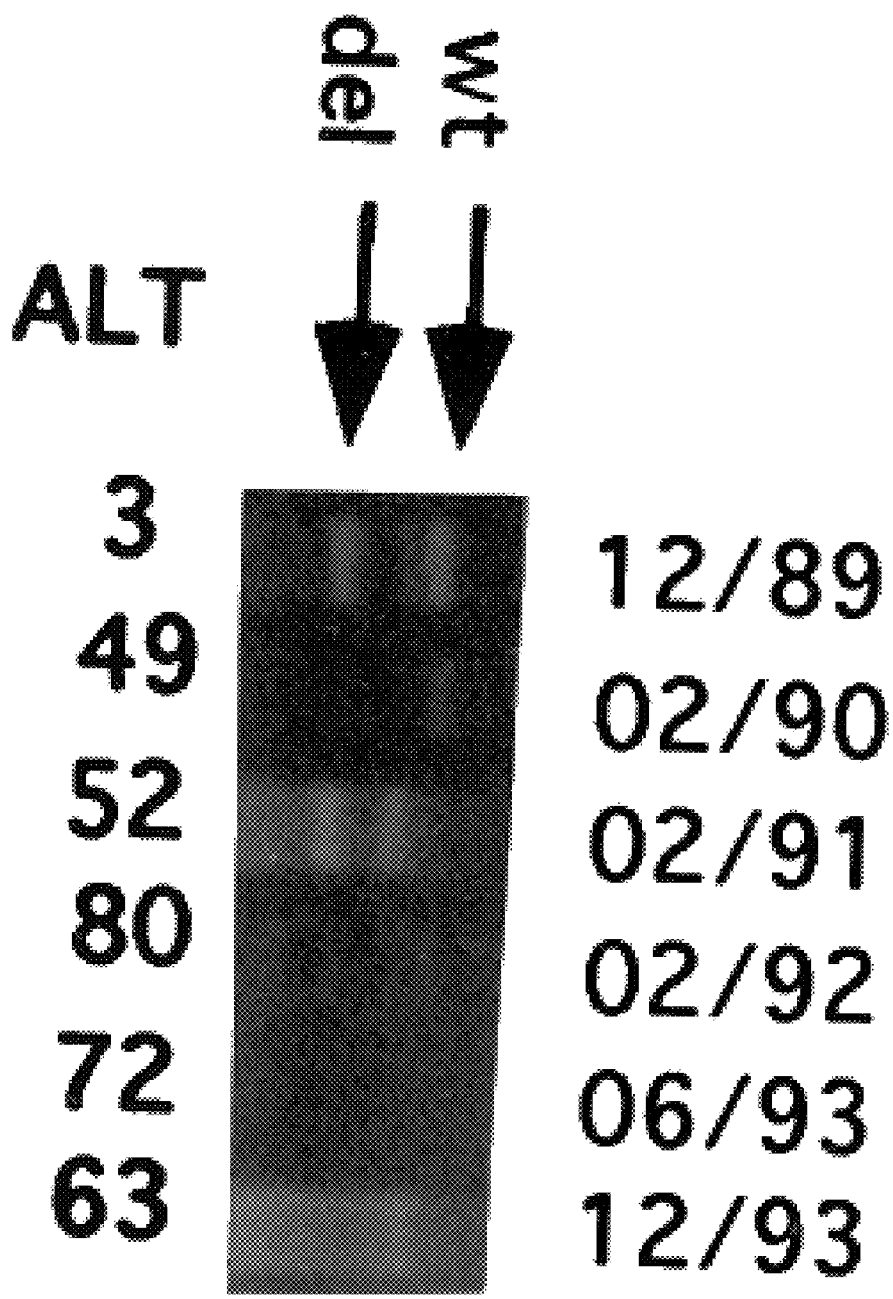

EXAMPLE 18
Cyclic Interactions in vivo between Helper Virus and defective interfering Particles Although the DEL85 and DEL109 constructs are faithful facsimiles of the original CID variants isolated from human patients in nature, these studies were based on tissue culture cell lines. To see if there is any dynamic equilibrium between the defective interfering and helper HBV in nature, HBV populations were examined in serially collected serum samples of a chronic active hepatitis patient. This patient (KP) died of HBV-related liver cancer and was followed up longitudinally from 1989 to 1993 at Fox Chase Cancer Center. Except for the samples collected in February 1992 and June 1993, HBV DNA can be detected in the sera of this patient via PCR (FIG. 7A). The relative abundance of helper and defective interfering viruses appears to be variable at different times. For example, only wild type, but not defective interfering viruses, were detectable in February 1990 and December 1993. However, both wild type and defective interfering mutations were detected in December 1989 and February, 1991.

To confirm the PCR data, DNA sequencing of 2–4 independent HBV clones from serum samples collected at different time points was performed. Two different CID mutants in FIG. 7B (clone 3 from December 1989 and clone 4 from February 1991) bears identical deletion endpoints to those of mutant DEL85. An out-of-frame internal deletion of core protein was also identified from clone 4 of December 1989. There is no correlation between the populations of either defective interfering or helper viruses and the clinical marker of liver injury (ALT) (FIG. 7A). Unlike the helper viruses, CID mutants, including DEL85, clone 3 of Dec/89, and clone 4 of Dec/93, did not accumulate any putative immune escape mutations at codon 13 within the hotspot mutational domain I. Nor did they accumulate any hotspot mutation at codon 151 of domain VI and codon 182 of domain VII (FIG. 7B; Hosono et al., '95). The wax and wane of defective interfering HBV from time to time was reminicent of the reported cycling phenomenon between defective interfering and helper viruses in other viral systems using tissue culture and animal models.

Despite the ubiquity and prevalence of HBV CID mutants in various hepatitis B carriers, the biological significance of CID mutants remain unclear. Two different CID mutants (DEL85 and DEL109) isolated from two different patients using two different hepatoma cell lines (Huh7 and HepG2) were characterized. CID mutants behave like defective interfering particles: deleted genome, replication defective, rescuable by standard helper virus, interfering with standard virus and enrichment of defective interfering particles. The interference effect is 3–16 fold in a single cycle, depending on the specific defective interfering virus per se, the host cell lines, and the relative dose of defective interfering and helper viruses. This effect could in theory become dramatized exponentially after a few serial cycles of infection.

As a DNA virus, hepadnaviruses can replicate through a pregenomic RNA intermediate (Summers & Mason, '82). Thus, hepadnaviruses have a unique phylogenetic status between DNA and RNA viruses. Although defective interfering viruses have been found in tissue culture or animal model of DNA and RNA viruses, the prevalent CID mutants of HBV characterized here are the first example of defective interfering-like particles in this hepadnaviridae family. To date, there have been no reports of defective interfering particles found in human infections in nature (Holland '87 and '91).

The conventional approach of defective interfering particles relies on the plaque assay via infection in tissue culture or passage in animal models. Although in vitro infection assay of HBV has been reported, it is still not generally adopted by most HBV research laboratories. The present invention demonstrates a new approach to defective interfering studies without relying on the conventional infection and plaque assays.

EXAMPLE 19
Mechanism of Occurrence of Core Internal Deletion

The occurrence of CID mutants is not due to the reverse transcription of spliced HBV-specific RNA (Terre '91). First, none of the deletional endpoints have the consensus sequences required for RNA splice donor and acceptor sites (i.e., GT and AG rule). Second, the deletion end points are variable in positions (Okamoto et al., 87; Wakita et al., '91; Ackrill et al., '93). Third, the deletion endpoints do not coincide with any of the reported splice junctions in HBV literature (Chen et al., '89). There is a 2–3 nucleotide junctional homology at both ends of internal deletion of several CID variants. This result is more in line with a mechanism of intramolecular illegitimate recombination (Shih et al., '87).

EXAMPLE 20
Mechanism(s) of Enrichment and Interference

One mechanism of the defective interfering phenomenon is the induced production of interferon by defective interfering particles, as was reported in influenza viruses. As demonstrated herein, the defective interfering phenomenon in HBV is not due to nonspecific cytotoxicity, nor is it due to production of interferon or other unknown soluble factors (FIGS. 5A and 5B).

It remains unclear if the mechanisms of HBV-defective interfering enrichment and interference are related or independent. If they are independent, they may be caused by two or more separate mutations or by a single pleiotropic mutation. In the constructions of plasmids pDEL85 and pDEL109, a 1 kb SspI fragment of CID mutants was amplified and subcloned into the backbone of a wild type HBV plasdmid. Therefore, the defective interfering phenotype of CID mutants is encoded entirely within this 1 kb fragment. When the amino acid sequences of this 1 kb insert of DEL85 and DEL109 were compared, the only common mutations between these two different CID mutants was the core internal deletion as well as an A-to-T change and a G-to-A change at nucleotide 1762 and 1764 respectively (referred to as TA mutations). The TA mutations occurring within the basal core promoter/X gene have been found in patients with chronic hepatitis, fulminant hepatitis and hepatocellular carcinomas. TA mutants are replication competent and might replicate slightly better than wild type (Buckwold et al., '96). The modest effect of TA mutation on the replication of HBV cannot explain for the interference of up to a 16 fold effect.

When the deleted core protein alone was provided to the wild type HBV, no apparent negative effect on the replication of wild type HBV was observed (FIG. 6F). There is also no negative effect from the CID mutant at the level of transcription. Taken together, the defective interfering phenotype of HBV CID mutants appears to be caused mainly by a single deletional mutation and no detectable negative effect is involved in the interference. Interference of HBV-CID mutants may be secondary to enrichment.

Figure 7B:
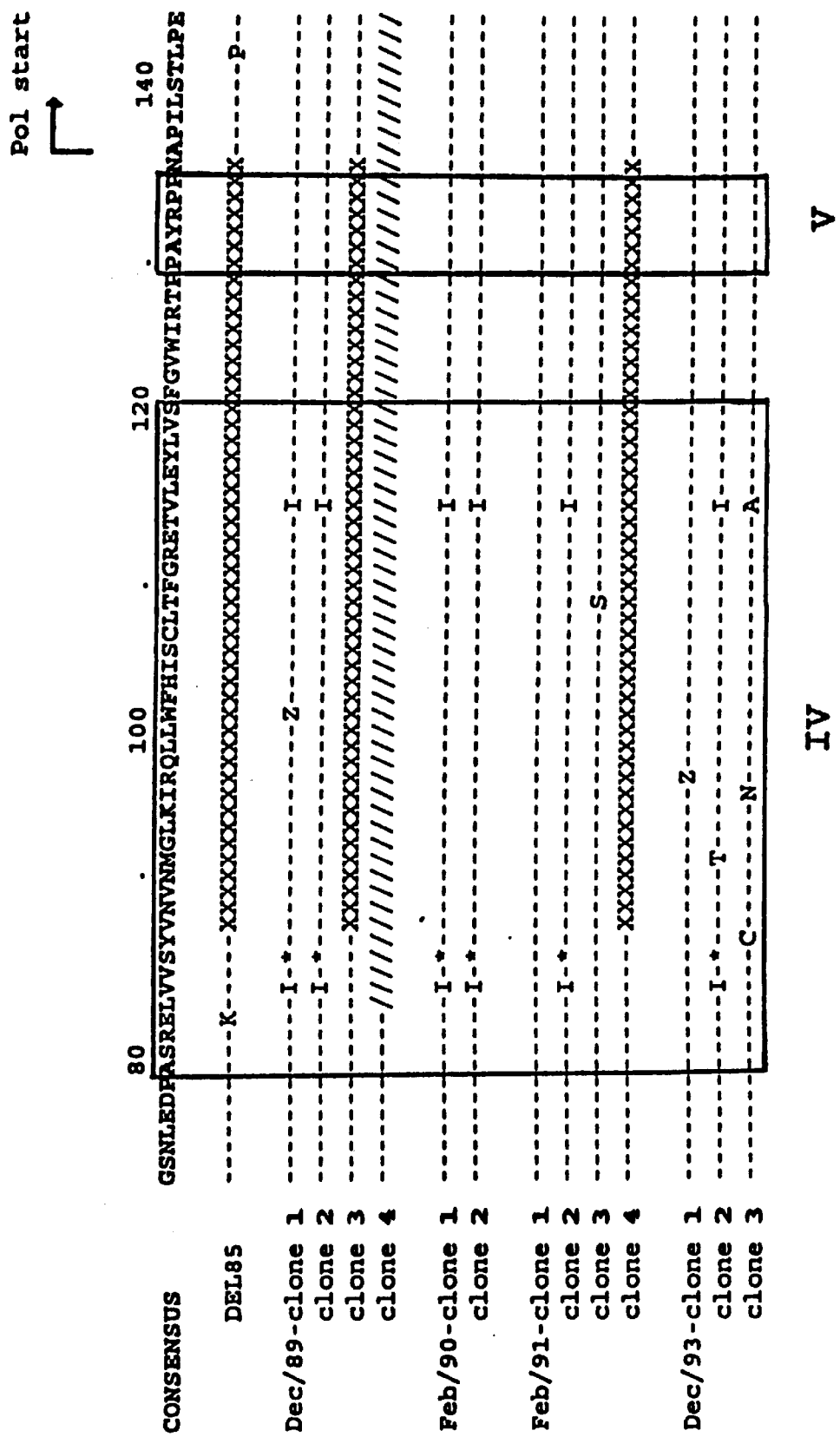
Figure 7C:
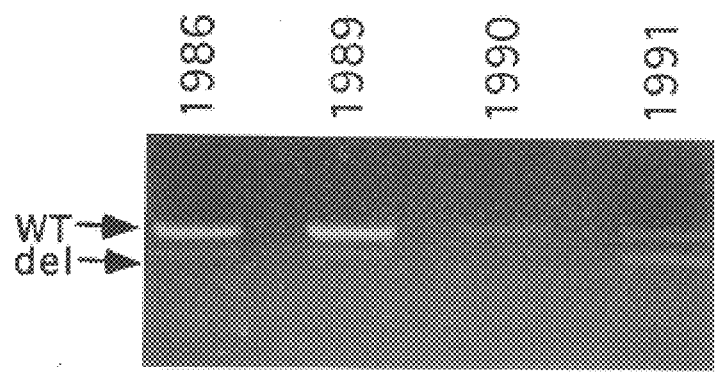
Figure 7D:
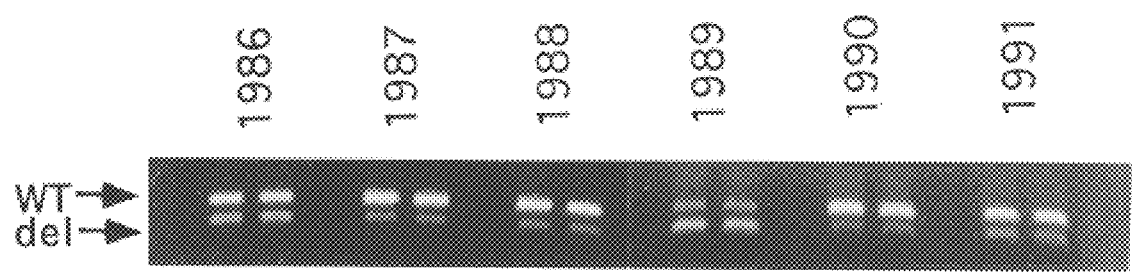
Figure 8:
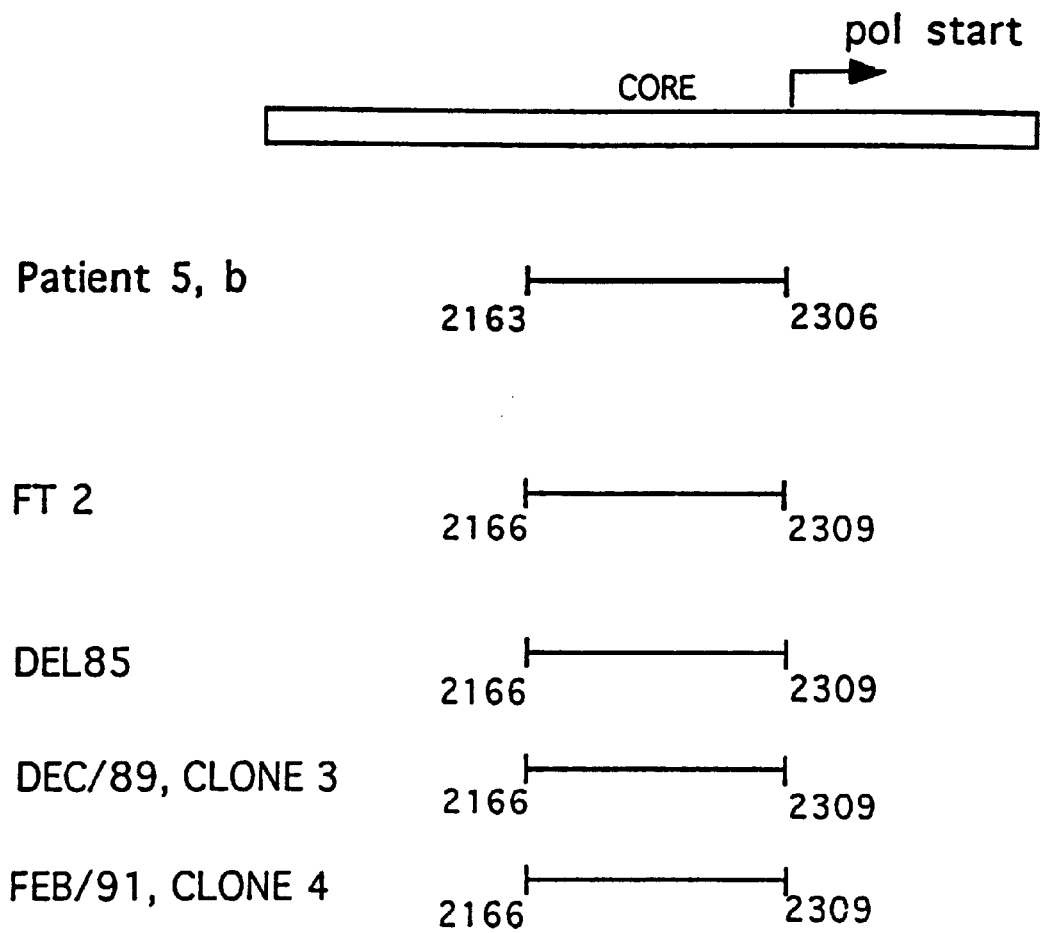
Figure 9:
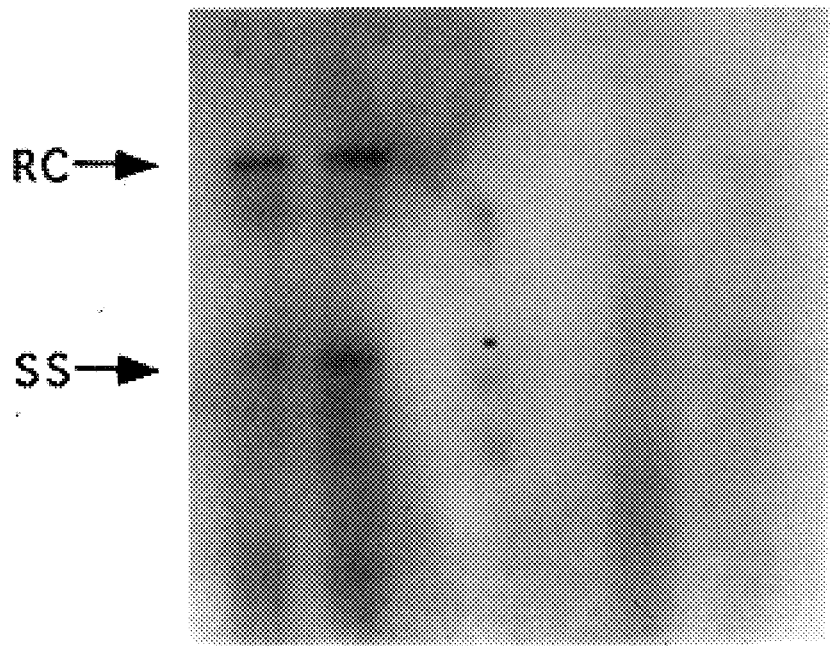

EXAMPLE 21
Multiple Immune Escape Mutations and defective interfering-Immune Shelter Hypothesis As described earlier, the deleted core protein is highly unstable in vivo (FIG. 6). This result led to the hypothesis that the deleted core protein often gets degraded soon after synthesis without ever being presented to the immune system as a target antigen. This hypothesis is supported by the previous observation that CID mutants T61 and T109, accumulated no mutation in the other known hotspot mutational domains of core antigen (Hosono et al., '95). By contrast, late stage helper virus variants generally accumulate an average of 4 mutational domains in HBcAg (Hosono et al., '95). This result is reinforced by the present invention that three additional clones of CID mutants from two different patients also contain no mutation in other mutational domains (FIG. 7B). Taken together, 5 different CID clones from 4 different patients accumulated a total of zero mutations, instead of the predicted total of 12 mutations, in the other hotspot mutational domains of HBcAg. Therefore, the deleted core proteins of CID mutants appear to ignore the immune selective pressure and can be considered as "immunologically anergic".

When lymphocytic choriomeningitis virus (LCMV) was injected into transgenic mice bearing a LCMV-specific T cell receptor (TCR), LCMV variants containing immune escape mutations within the cytotoxic T lymphocyte (CTL) epitope were found to prevail from evolution. Although immune escape mutations of LCMV were possible in this artificial animal model which bears a monospecific TCR, it is unclear how could multiple independent immune escape mutations occur simultaneously in the field within multiple epitopes of multiple viral antigens concurrently under immune surveillance. For example, there are an average of 4 different putative immune escape mutations within different HLA-class II-restricted T cell epitopes of HBV core antigen (Hosono et al., '95). Similarly, at least four different mutations at four topographically distinct antibody recognition sites on the three-dimentional structure of the influenza haemagglutinin have been proposed as a requirement for the production of new epidemic strains between 1968 and 1975 (Wiley et al., '81; Caton et al., '82). The internal deletion of CID mutants only deleted one, sometimes two, of the four potentially important T cell epitopes (FIG. 7B; Jung et al., '95; Hosono et al., '95; Tsai et al., '96). Since the occurrence of mutations is always a rare event, to date, it is unknown whether the statistically unlikely occurrence of multiple immune escape mutations of viruses could actually occur in nature under the host's multispecific immune system.

To look for a similar phenomenon in natural HBV infections, serum samples were collectedfrom three chronic carriers during a longitudinal study and found the deleted core mutation in HBV by PCR. The deletions in these DNA fragments were found to occur in the central part of HbcAg via sequencing. Furthermore, in the case of a Korean patient, the same CID variant population appeared to predominate during the 4 year follow-up period. The total HBV DNA titer was seen to fluctuate over time and somtimes even dropped to a very low or undetectable level (FIG. 7C). Interestingly, the relative abundance of CID variants and helper viruses also appeared to vary over time. The relative intensity of helper virus-specific DNA was often greater than that of the CID variant DNA. However, at some time points, the reverse was observed (FIG. 7C, in 1991; FIG. 7D, in 1989). It should be mentioned here that in FIGS. 7C, and 4D, the absolute amount of the PCR product was not measured. Rather, the ratios between the wild type and CID variant populations at different time points were compared. Therefore, the quantity of each band is internally controlled by the other band.

These results indicate that a dynamic equilibrium could exist between the CID and helper HBV in vivo. This observed waxing and waning of DI-like and helper viruses are reminiscent of the cycling phenomenon reported in other DI viral systems, such as rabies and vesicular stomatitis virus (VSV) (21, 29).

Defective interfering particles were often found in cultures persistently infected with virulent viruses. The attenuating effect of defective interfering particles on the titer of helper viruses should provide the parental helper virus an advantage in establishing or maintaining persistent infection. Since HBV is not directly cytopathic to hepatocytes, the symbiotic relationship between defective interfering and helper HBV is different from previously reported defective interfering particles in other viruses (Holland '87). The present invention indicates that defective interfering particles could contribute to latency and chronicity of HBV infection by attenuating the replication of wild type helper viruses (FIGS. 3C, 3E, 3F) and subsequently decreasing the total amount of loaded wild type antigens to a subclinical level (which is) below the detection threshold of the hosts' immune surveillance. This hypothesis is supported by the finding that CID mutants are rarely (or never) found in acute hepatitis patients (Ehata et al., '93; Aye et al., '94), but are found in 100% of asymptomatic HBV carriers (Okamoto et al., '87), 64% of Japanese chronic hepatitis patients (Wakita et al., '91), 100% of HBV-infected kidney transplantation patients (Gunther et al., '95), and 75% of European Caucasian chronic active hepatitis (Ackrill et al., '93); however, in only 7% of chronic hepatitis B patients in Hongkong (Akarca and Lok '95). The discrepancy of the defective interfering prevalence between Hongkong and other places is unclear. It is possible that some of the HBV defective interfering viruses do not have deletion in HBcAg.

EXAMPLE 22

The in vivo cycling of variants in the Korean patient happens to contain a predominant CID variant population which shares an identical deletion with DEL85 and two other CID variants independently identified by two other research groups (see FIG. 8). Despite the identical CID deletion in the core region, DEL85 and the CID variants in the Korean patient are different from each other in the non-deleted portion by a total of 6 amino acids (data not shown). Thus, PCR contamination between DEL85 and the Korean sample is highly unlikely. In summary, the behavior of the cloned variant DEL85 probably can be directly related to the in vivo cycling data. Finally, according to the definition of cycling, the ratio between helper and DI particles does not remain constant. Depending on the timing of the sampling, the ratio between helper and DI viruses is expected to vary.

FIG. 9 shows the transfection of DEL85 plasmid DNA with a wild type core protein expression vector (pSVC) at a 10:1 DNA mass ratio into rat Morris hepatoma cell line 7777 or Q7. A total of 30 neomycin resistant colonies were selected from the transfected culture. After screening for active HBV DNA replication by Southern blot analysis, two independent clones (designated as DEL85/Q7 clones 1-15-1 and 1-12-2), producing the putative DEL85 HBV replication. Thus, the present invention demonstrates that one can produce a stable cell line producing defective interfering particles of viral origin. Furthermore, one can now purify defective interfering particles to homogeneity that are free from contamination of the replication competent helper virus.

Ackrill A M, Naoumov N V, Eddleston A L W F, and R. Williams, 1993, Specific deletions in the hepatitis B virus core open reading frame in patients with chronic active hepatitis B. *J. Med. Virol.* 41:165–169.

Akarca U S and Lok A S F. 1995. Naturally occurring core-gene-defective hepatitis B viruses. *J. Gen. Virol.* 76:1821–1826.

Aye, T. T., Uchida, T., Becker, S. O., Hirashima, M., Shikata, T., Komine, F., Moriyama, M., Arakawa, Y., Mima, S., Mizokami, M., and Lau, J. Y. N. 1994. Variations of hepatitis B virus precore/core gene sequence in acute and fulminant hepatitis B. *Digestive Diseases and Sciences* 39:1281–1287.

Bozkaya H, Ayola B, and Lok A S F. 1996. High rate of mutations in the hepatitis B core gene during the immune clearance phase of chronic hepatitis B virus infection. *Hepatology* 24:32–37.

Buckwold V E, Xu Z, Chen M, Yen T S B, and Ou J H. 1996. Effects of a naturally occurring mutation in the hepatitis B virus basal core promoter on precore gene expression and viral replication. *J. Virol.* 70:5845–5851.

Carman, W. F., M. R. Jacyna, S. Hadziyannis, P. Karayiannis, M. J. McGarvey, A. Makris and H. C. Thomas. (1989). Mutation preventing formation of hepatitis B e antigen in patients with chronic hepatitis B infection. *Lancet* ii:588–591.

Caton A J, Brownlee G G, Yewdell J W and Gerhard W. 1982. The antigenic structure of the influenza virus A/PR/8134 Hemagglutinin (Hi subtype). *Cell* 31:417–427.

Chen P J, Chen C R, Sung J L, and Chen D S. 1989. *J. Virol.* 63:4165–4171.

Chisari et al., Hepatitis B virus immunopathogenesis. *Annu Rev Immunol* 1995;13:29–60.

Dimmock, N J. 1996. Antiviral activity of defective interfering influenza virus in vivo, in: Viral and Other Infections of the Human Respiratory Tract. (S. Myint and D. Taylor-Robinson, eds.), chapter 22, p. 421–445.

Ehata, T., M. Omata, W-L. Chuang, O. Yokosuka, Y. Ito, K. Hosoda, and M. Ohto. (1993). Mutations in core nucleotide sequence of hepatitis B virus correlate with fulminant and severe hepatitis. *J. Clin. Invest.* 91:1206–1213.

Field J., Nikawa J I, Broek D, McDonald B, Rodgers L, Wilson I A, Lerner R A and M. Wigler. 1988. Purification of a ras-responsive adenylyl cyclase complex from Saccharomyces cerevisiae by use of an epitope addition method. *Mol. Cell. Biol.*

Gallina, A., F. Bonelli, L. Zentilin, G. Rindi, M. Muttini, and G. Milanesi. 1989. A recombinant hepatitis B core antigen polypeptide with the protamine-like domain deleted self-assembles into capsid particles but fails to bind nucleic acids. *J. Virol.* 63:4645–4652.

Gunther S., Li B C, Miska S., Kruger D H, Meisel H., and Will H. 1995. A novel method of efficient amplification of whole hepatitis B virus genomes permits rapid functional analysis and reveals deletion mutants in immunosuppressed patients. *J. Virol.* 69:5437–5444.

Hatton, T., S. Zhou, and D. N. Standring. 1992. RNA- and DNA-binding activities in hepatitis B virus capsid protein: a model for their roles in viral replication. *J. Virol.* 66:5232–5241.

Holland J J. 1987. Defective interfering rhabdoviruses. in: The Rhabdoviruses. (R. Wagner, ed.), p. 297–360, Plenum Publishing Co., New York.

Hosono S, Tai P-C, Wang W, et al. Core antigen mutations of human hepatitis B virus in hepatomas accumulate in MHC class II-restricted T cell epitopes. *Virology* 1995;212:151–162.

Huang, A. S. and Baltimore, D., 1970, Defective viral particles and viral disease processes, *Nature* (London) 226:325.

Huang, A. S. and Baltimore, D., 1977, Defective interfering animal viruses, in *Comprehensive Virology*, vol. 10 (H. FraenkelConrat and R. R. Wagner, eds.), p. 73–116, Plenum Press, New York.

Jung M C, Diepolder H M, Spengler U, Wierenga E A, Zachoval R, Hoffmann R M, Eichenlaub D, Frosner G, Will H, and G R Pape. 1995. Activation of a heterologous hepatitis B (HB) core and e antigen-specific CD4+ T-cell population during seroconversion to anti-HBe and anti-HBs in hepatitis B virus infection. *J. Virol.* 69:3358–3368.

Lee Y I, Hur G M, Suh D J, and Kim S H. 1966. Novel preC.C gene mutants of hepatitis B virus in chronic active hepatitis: naturally occurring escape mutants. *J. Gen. Virol.* 77:1129–1138.

Milich, D. R., A. McLachlan, A. Moriarty, G. B. Thornton. (1987). Immune response to hepatitis B virus core antigen (HBcAg): Localization of T cell recognition sites within HBcAg/HBeAg. *J. of Immunology* 139:1223–1231.

Milich, D. R., J. E. Jones, J. L. Hughes, J. Price, A. K. Raney, and A. McLachlan. (1990). Is a function of the secreted hepatitis B e antigen to induce immunologic tolerance in utero? *Proc. Natl. Acad. Sci. USA* 87:6599–6603.

Milich, D. R., A. McLachlan, A. Moriarty, G. B. Thornton. (1987). Immune response to hepatitis B virus core antigen (HBcAg): Localization of T cell recognition sites within HBcAg/HBeAg. *J. of Immunology* 139:1223–1231.

Ono, Y., H. Onda, R. Sasada, K. Igarashi, Y. Sugino, and K. Nishioka. (1983). The Complete Nucleotide Sequences of The Cloned Hepatitis B Virus DNA: Subtype adr and adw. *Nucleic Acids Res.* 11:1747–1757.

Penna, A., A. Bertoletti, A. Cavalli, A. Valli, G. Missale, M. Pilli, S. Marchelli, T. Giuberti, P. Fowler, F. V. Chisari, F. Fisccadori, and C. Ferrari. (1992). Fine specificity of the human T cell response to hepatitis B virus core antigen. *Arch. Virol.* 4:23–28.

Phillips, R. E., S. Rowland-Jones, D. F. Nixon, F. M. Gotch, J. P. Edwards, A. O. Ogunlesi, J. G. Elvin, J. A. Rothbard, C. R. M. Bangham, C. R. Rizza, and A. J. McMichael. (1991). Human immunodeficiency virus genetic variation that can escape cytotoxic T cell recognition. *Nature* 354:453.

Mondelli, M., G. M. Vergani, A. Alberti, D. Vergani, B. Portmann, A. L. W. F. Eddleston, and R. Williams.(1982). Specificity of T lymphocyte cytotoxicity to autologous hepatocytes in chronic hepatitis B virus infection: Evidence that T cells are directed against HBV core antigen expressed on hepatocytes. *J. of Immunology* 129: 2773–2778.

Okamoto, H., F. Tsuda and M. Mayumi. (1987). Defective Mutants of Hepatitis B Virus in the Circulation of Symptom-Free Carriers. Japan. *J. Exp. Med.* 57:217–221.

Okamoto, H., F. Tsuda, H. Sakugawa, R. I. Sastrosoewignjo, M. Imai, Y. Miyakawa, and M. Mayumi. (1988). Typing Hepatitis B virus by homology in nucleotide sequence: comparison of surface antigen subtypes. *J. Gen. Virol.* 69:2575–2583.

Okamoto H, Tsuda F, Akahane T, et al. Hepatitis B virus with mutations in the core promoter for an e antigen-negative phenotype in carriers with antibody to e antigen. *J. Virol.* 1994; 68:8102–8110.

Pircher, H., D. Moskophidis, U. Rohrer, K. Buirki, H. Hengartner, and R. M. Zinkernagel. (1990). Viral escape by selection of cytotoxic T cell-resistant virus variants in vivo. *Nature* 346:629.

Roux, L., Simon A E, and Holland J J. 1991. Effects of defective interfering viruses on viral replication and pathogenesis in vitro and in vivo. *Adv. Virus Res.* 40:181–211.

Roychoudhury S, Faruqi A, Shih C. Pregenomic RNA encapsidation analysis of eleven missense and nonsense polymerase mutants of human hepatitis B virus. *J Virol* 65: 3617–3624, 1991.

Sato S, Suzuki K, Akahane Y, et al. Hepatitis B virus strains with mutations in the core promoter of patients with fulminant hepatitis. *Ann. Int. Med.* 1995; 122:241–248.

Salfeld, J., E. Pfaff, M. Noah, and H. Schaller. (1989). Antigenic determinants and functional domains in core antigen and e antigen from hepatitis B virus. *J. Virol.* 63(2):798–808.

Scaglioni P P, Melegari M, and J R Wands. 1994. Characterization of hepatitis B virus core mutants that inhibit viral replication. *Virology* 205:112–120.

Shih C, Tai P-C, Whitehead W, Hosono S, Lee C-S, Yang C-S. 1996. Hepatitis B and C viruses and liver cancer. in: Encyclopedia of Cancer. Academic Press, Inc. (in press).

Summers, J. and W. S. Mason. (1982). Replication of the genome of a hepatitis B-like virus by reverse transcription of an RNA intermediate. *Cell* 29:403–415.

Shih, C., K. Burke, J. Zeldis, J. Wands, K. J. Isselbacher, M. J. Chou, C. S. Yang, C. S. Lee, and H. M. Goodman. (1987). Tight clustering of human hepatitis B virus integration sites in hepatomas near a 'Triple-stranded' region. *J. Virol.* 61:3491–3498.

Terre S, Petit M A, and Brechot C. 1991. Defective hepatitis B virus particles are generated by packaging and reverse transcription of spliced viral RNAs in vivo. *J. Virol.* 65:5539–5543.

Tsai, S. L., P. J. Chen, M. Y. Lai, P. M. Yang, J. L. Sung, J. H. Huang, L. H. Hwang, T. H. Chang and D. S. Chen. (1992). Acute Exacerbations of chronic type B hepatitis are accompanied by increased T cell responses to hepatitis B core and e antigens. *J. Clin. Invest.* 89:87–96.

Tsai S L, Chen M H, Yeh C T, Chu C M, Lin A N, Chiou F H, Chang T H, and Y F Liaw. 1996. Purification and characterization of a naturally processed hepatitis B virus peptide recognized by CD8+ cytotoxic T lymphocytes. *J. Clin. Invest.* 97:577–584.

Vento, S., J. E. Hegarty, A. Alberti, C. J. O'Brien, G. J. M. Alexander, A. L. W. F. Eddleston and R. Williams.(1985). T-lymphocyte sensitization to HBcAg and T cell-mediated unresponsiveness to HBsAg in hepatitis B virus-related chronic liver disease. *Hepatology* 5:192–197.

von Magnus, P., 1947, Studies on interference in experimental influenza. Biological observations, *Ark. Kemi. Mineral. Geol.*, 24(7):1.

Wiley D C, Wilson I A, and Skehel J J. 1981. Structural identification of the antibody-binding sites of Hong Kong influenza haemagglutinin and their involvement in antigenic variation. *Nature* 289:373–378.

Wakita, T., S. Kakumu, M. Shibata, K. Yoshioka, Y. Ito, T. Shinagawa, T.Ishikawa, M. Takayanagl, and T. Morishima. (1991). Detection of pre-C and core region mutants of hepatitis B virus in chronic hepatitis B virus carriers. *J. Clin. Invest.* 88:1793–1801.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A defective interfering particle of hepadnaviruses, wherein said particle has the following characteristics: replication defective, rescuability by helper viruses, interference of helper virus, and enrichment of defective interfering particles.

2. The defective interfering particle of claim 1, wherein said hepadnavirus is human Hepatitis B virus.

3. The defective interfering particle of claim 1, wherein said particle has a mutation of hepadnavirus core antigen.

4. The defective interfering particle of claim 3, wherein said particle has a deletion of approximately amino acids 88–135 of Hepatitis B core antigen.

5. The defective interfering particle of claim 4, wherein said particle is DEL85.

6. The defective interfering particle of claim 3, wherein said particle has a deletion of approximately amino acids 82–122 of Hepatitis B core antigen.

7. The defective interfering particle of claim 6, wherein said particle is DEL109.

8. A pharmaceutical composition, comprising the defective interfering particle of claim 3 and a pharmaceutically acceptable carrier.

9. An immunogenic composition, comprising the defective interfering particle of claim 3.

* * * * *